(12) United States Patent
Nomura et al.

(10) Patent No.: US 12,217,619 B2
(45) Date of Patent: *Feb. 4, 2025

(54) HABIT IMPROVING DEVICE, METHOD AND RECORDING MEDIUM

(71) Applicant: OMRON Corporation, Kyoto (JP)

(72) Inventors: Taisuke Nomura, Nara (JP); Keiichi Obayashi, Tokyo (JP); Seitaro Mura, Kyoto (JP)

(73) Assignee: OMRON Corporation, Kyoto (JP)

( * ) Notice: Subject to any disclaimer, the term of this patent is extended or adjusted under 35 U.S.C. 154(b) by 773 days.

This patent is subject to a terminal disclaimer.

(21) Appl. No.: 17/270,851

(22) PCT Filed: Mar. 8, 2019

(86) PCT No.: PCT/JP2019/009252
§ 371 (c)(1),
(2) Date: Feb. 23, 2021

(87) PCT Pub. No.: WO2020/100319
PCT Pub. Date: May 22, 2020

(65) Prior Publication Data
US 2021/0241651 A1 Aug. 5, 2021

(30) Foreign Application Priority Data
Nov. 14, 2018 (JP) ................. 2018-214042

(51) Int. Cl.
*G09B 19/00* (2006.01)
*G16H 50/70* (2018.01)
(Continued)

(52) U.S. Cl.
CPC ............. *G09B 19/00* (2013.01); *G16H 50/70* (2018.01); *G01C 22/006* (2013.01);
(Continued)

(58) Field of Classification Search
CPC ........ G09B 19/00; G16H 50/70; G16H 20/30; G16H 20/60; G16H 40/67; G16H 50/20; G01C 22/006; G06Q 10/109
(Continued)

(56) References Cited

U.S. PATENT DOCUMENTS

| | | | | |
|---|---|---|---|---|
| 2007/0173705 A1* | 7/2007 | Teller | ...................... | A61B 5/681 600/595 |
| 2010/0075807 A1* | 3/2010 | Hwang | .................. | G06Q 90/00 482/8 |

(Continued)

FOREIGN PATENT DOCUMENTS

| | | |
|---|---|---|
| CN | 105590022 | 5/2016 |
| CN | 107924550 | 4/2018 |

(Continued)

OTHER PUBLICATIONS

"Office Action of Europe Counterpart Application", issued on Aug. 24, 2023, p. 1-p. 13.

(Continued)

*Primary Examiner* — Jack Yip
(74) *Attorney, Agent, or Firm* — JCIPRNET

(57) ABSTRACT

This habit improving device is provided with: a first calculation unit which, for every first period, acquires an activity amount of the user totaled for each first period, and which calculates a distribution pattern that indicates the change over time in the activity amount during a second period, which includes a first period; a sorting unit which classifies multiple of the distribution patterns into one or more groups; a second calculation unit which, on the basis of attribute information relating to the user's attributes, and external factor information relating to external factors, which are factors affecting the user by matters outside of the user, calculates, and associates with the groups, a target pattern as a target for the user; and a presenting unit which presents (Continued)

advice information to the user on the basis of the current distribution pattern and the target pattern.

10 Claims, 14 Drawing Sheets

(51) Int. Cl.
    *G01C 22/00*     (2006.01)
    *G06Q 10/109*     (2023.01)
    *G16H 20/30*     (2018.01)
    *G16H 20/60*     (2018.01)
    *G16H 40/67*     (2018.01)
    *G16H 50/20*     (2018.01)

(52) U.S. Cl.
    CPC ........... *G06Q 10/109* (2013.01); *G16H 20/30* (2018.01); *G16H 20/60* (2018.01); *G16H 40/67* (2018.01); *G16H 50/20* (2018.01)

(58) Field of Classification Search
    USPC ......................................................... 434/236
    See application file for complete search history.

(56) References Cited

U.S. PATENT DOCUMENTS

| | | | |
|---|---|---|---|
| 2013/0158368 A1* | 6/2013 | Pacione | A61B 5/318 600/595 |
| 2014/0039840 A1* | 2/2014 | Yuen | H04W 4/029 702/189 |
| 2014/0228649 A1* | 8/2014 | Rayner | A61B 5/0002 600/595 |
| 2014/0276244 A1* | 9/2014 | Kamyar | A61B 5/0205 600/595 |
| 2015/0324751 A1* | 11/2015 | Orenstein | G16H 40/67 702/3 |
| 2017/0014068 A1* | 1/2017 | Gotoh | A61B 5/1118 |
| 2017/0188864 A1* | 7/2017 | Drury | A61B 5/02427 |
| 2018/0036591 A1* | 2/2018 | King | H04N 5/76 |
| 2018/0056130 A1* | 3/2018 | Bitran | A63B 24/0075 |
| 2018/0107793 A1* | 4/2018 | Ni | G16H 20/00 |

FOREIGN PATENT DOCUMENTS

| | | |
|---|---|---|
| CN | 108348813 | 7/2018 |
| EP | 3886106 | 9/2021 |
| JP | 2004121745 | 4/2004 |
| JP | 2008117174 | 5/2008 |
| JP | 2011242858 | 12/2011 |
| JP | 2014182611 | 9/2014 |
| JP | 5772113 | 9/2015 |
| JP | 2017000455 | 1/2017 |
| JP | 2017097401 | 6/2017 |
| JP | 2018010446 | 1/2018 |
| WO | 2010146811 | 12/2010 |
| WO | 2011070831 | 6/2011 |

OTHER PUBLICATIONS

Office Action of China Counterpart Application, with English translation thereof, issued on Aug. 31, 2023, pp. 1-27.
Jimsreviewroom, "Garmin Vivofit 3—Review", May 2016, retrieved from https : //www.youtube.com/watch?v=70Zf9Bm8at4.
Garmin Connect Web—Mobile Apps & Web—Garmin Forums, "How does auto goal work?", Aug. 2016, retrieved on May 2022, from : https://forums.garmin.com/apps-software/mobile-apps-web/f/garmin-connect-web/117509/how-does-auto-goal-work.
"Search Report of Europe Counterpart Application", issued on Jun. 17, 2022, pp. 1-11.
"International Search Report (Form PCT/ISA/210)" of PCT/JP2019/009252, mailed on May 21, 2019, with English translation thereof, pp. 1-4.
"Written Opinion of the International Searching Authority (Form PCT/ISA/237)" of PCT/JP2019/009252, mailed on May 21, 2019, with English translation thereof, pp. 1-12.

* cited by examiner

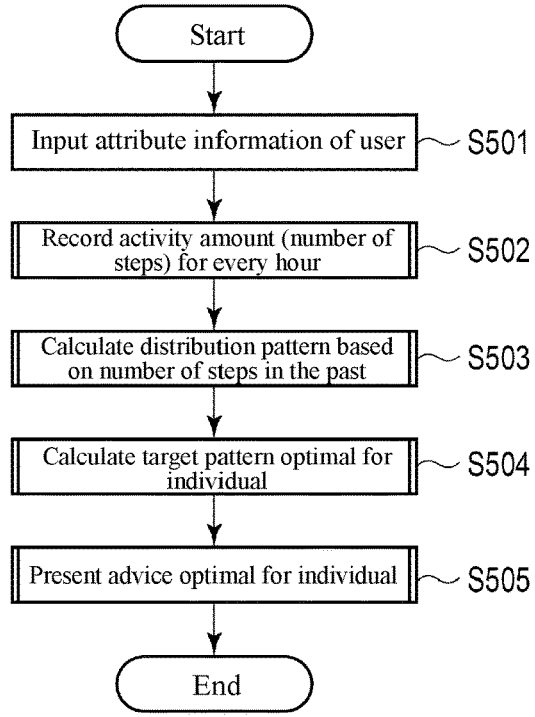
FIG. 5
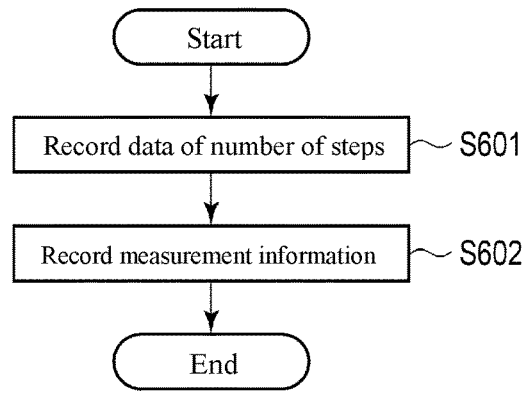
FIG. 6A
| User_ID | Year | Month | Day | Day of the week | Time | Number of steps |
|---|---|---|---|---|---|---|
| 98765 | 20XX | 1 | 1 | Monday | 12:00 | 123 |
| 98765 | 20XX | 1 | 1 | Monday | 13:00 | 14 |
| 98765 | 20XX | 1 | 1 | Monday | 14:00 | 0 |
| 98765 | 20XX | 1 | 1 | Monday | 15:00 | 2186 |
| ⋮ | ⋮ | ⋮ | ⋮ | ⋮ | ⋮ | ⋮ |
FIG. 6B

HABIT IMPROVING DEVICE, METHOD AND RECORDING MEDIUM

CROSS-REFERENCE TO RELATED APPLICATION

This application is a 371 application of the International PCT application serial no. PCT/JP2019/009252, filed on Mar. 8, 2019, which claims the priority benefits of Japan Patent Application No. 2018-214042, filed on Nov. 14, 2018. The entirety of each of the above-mentioned patent applications is hereby incorporated by reference herein and made a part of this specification.

TECHNICAL FIELD

This invention relates to a habit improving device, a method, and a program recording medium.

RELATED ART

Recently, there has come to be many people (who will be referred to as users) who are under pressure to improve their lifestyle habits due to results from medical examinations or the like. For example, users may be warned of a high probability that they will suffer from lifestyle habits-related illnesses in the future or they may already be suffering from such illnesses on the occasion of medical examinations or the like held by his/her workplace or local government. For example, in such a case, users may plan to change their daily life in order to improve their lifestyle habits by seeking the guidance of specialists or utilizing professional application software or the like. These plans include designing daily life such that the amount of food eaten is reduced in a diet, the kinds of food and drink are changed, and an exercise time is increased, for example, according to reviewing current lifestyle habits in accordance with the symptoms of warned of illness.

In order to measure an exercise time, for example, a pedometer may be utilized. A pedometer is a device for measuring the number of steps by detecting oscillations or the like of a human body and is mainly utilized as healthcare equipment. There are pedometers having a function of calculating and displaying a walking distance, a walking speed, consumed calories, and the like from the count value of the number of steps, and change in movement or posture of the human body, or the like, in addition to the number of steps. Using equipment having these functions, for example, the remaining number of steps at the current time with respect to a daily target value of a total number of steps can be indicated for each user, and this is very convenient for users who intend to improve their lifestyle habits.

For example, Patent Literature 1 discloses a health support device providing optimal advice for a user to continue walking without hardship by evaluating the number of steps of the user based on the absolute number thereof or the amount of change thereof and further discloses a health support device providing more appropriate advice for a user regarding the counted number of steps focusing on evaluation of the level of the number of steps or change in quantity of steps and aiming to provide guidance for maintaining the health and health promotion of the user.

In Patent Literature 1, focusing on a method of evaluating the number of steps of a user, an evaluation method is used depending on the purpose between a case of judging a level of a quantity of steps during a certain recent period and providing advice corresponding to the level and a case of comparing an average number of steps before one elapsed time period and an average number of steps after one elapsed time period in the past to each other and providing advice including the amount of change therebetween. In addition, data is backed up, advisory sentences are updated or the like, and the evaluation method is changed in some cases by transmitting data of the number of steps to a server device via an information terminal.

CITATION LIST

Patent Literature

[Patent Literature 1]
  Japanese Unexamined Patent Application Publication No. 2004-121745

SUMMARY OF INVENTION

Technical Problem

A health support device in the related art provides advice or information optimal for conditions regarding the quantity of steps of a user by evaluating the level of the average number of steps during a certain recent period based on the counted number of steps of the user, or comparing the average number of steps before one elapsed time period and the average number of steps after one elapsed time period in the past for evaluation to each other and including the amount of change therebetween.

In this manner, regarding the number of steps of a user, devices in the related art merely provide advice or information to a user based on evaluation of the level of the average number of steps during a certain recent period or comparison between the average numbers of steps during different periods in the past for evaluation including the amount of change therebetween. For this reason, since activities other than walking in lifestyle habits of a user are not measured, and furthermore, since different factors other than walking affecting lifestyle habits of a user are not taken into account, lifestyle habits of a user may not be appropriately improved.

This invention has been made focusing on the foregoing circumstances, and in an aspect, in order to take into account both the user's activity amount and factors other than the activity amount to provide guidance for the user to have suitable lifestyle habits, a habit improving device, a method, and a program are provided.

Solution to Problem

In order to solve the foregoing problems, the present disclosure employs the following constitutions.

That is, according to a first aspect of the present disclosure, there is provided a habit improving device including a first calculation unit which acquires, for each of first periods, a user's activity amount totaled for each of the first periods and calculates a distribution pattern indicating change over time in the activity amount during a second period including the first periods; a sorting unit which sorts a plurality of the distribution patterns into one or more groups; a second calculation unit which calculates a target pattern that becomes a target for the user in association with the groups, based on attribute information relating to an attribute of the user and external factor information relating to an external factor that is a factor affecting the user due to a matter other than the user; and a presenting unit which presents advice information to the user based on the current distribution pattern and the target pattern.

In the foregoing constitution, the first calculation unit calculates the distribution pattern indicating change over time in the activity amount of the user throughout the second period and totals the activity amount for each of the first periods included in the second period. Therefore, the distribution pattern of the activity amount is obtained in units realized by dividing the second period for each of the first periods. Typically, for example, the first period is one hour, and the second period is one day. However, any period may be adopted as long as the first period is included in the second period. A plurality of distribution patterns obtained in this manner is sorted into one or more groups by the sorting unit. The sorting unit sorts the plurality of obtained distribution patterns using a certain technique. Examples of this technique for performing sorting include clustering and hierarchy sorting. Further, the second calculation unit acquires the attribute information of the user and the external factor information relating to an external factor (which will also be referred to as an outside factor, an external environment, and an outside environment) affecting the user and calculates the target pattern that should become a target for the user for each of the sorted groups based on the information.

Attribute information of the user is information relating to an attribute of the user and is information related to a matter regarding the user himself/herself. For example, it is information indicating a gender, date of birth, and residence of the user. In addition, external factor information of the user, which is different from the attribute information, is information relating to a matter other than those regarding the user and is information relating to an external factor affecting the user. Examples thereof include positional information indicating a current location of the user, weather forecast information corresponding to the positional information of the user, and information relating to a schedule of the user. Here, an external factor indicates influence from outside of the user, that is, an environment around the user. Since the second calculation unit performs calculation by associating the target pattern with the groups, the target pattern is calculated while taking the distribution patterns based on the activity amount of the user in the past into account. In other words, the second calculation unit calculates a target pattern desirable for the user in accordance with the attribute information of the user and the external factor affecting the user while taking features of the groups into account.

The presenting unit acquires the distribution patterns of the activity amounts based on current activities of the user and the calculated target pattern and presents current advice information for the user to the user from these patterns. A current distribution pattern indicates a distribution pattern from the beginning of a corresponding second period until the present. For example, it indicates a distribution pattern from the beginning of a day (for example, waking up in the morning) until the present (for example, 11 a.m. before lunch). The presenting unit compares this current distribution pattern (that is, history information of today's activity amount until the present) and the calculated target pattern to each other. For example, when today's activity amount until the present is smaller than the totaled activity amount of the target pattern, the presenting unit presents the advice information that the user should achieve a large activity amount from then on. In the opposite case, the presenting unit presents the advice information that the user can reduce the activity amount from that of the target pattern. The presenting unit may present the advice information to the user while taking an external factor such as a future schedule, and the attribute information into account.

Therefore, according to the present disclosure, the user can be informed of advice for coming closer to having ideal activity habits (for example, walking habits) taking an external factor into account, and thus it is easy to change over to a behavior of executing activity habits. In addition, according to the present disclosure, it is possible to calculate a more detailed target pattern for an individual for each of the first periods by sorting the activity amounts (for example, the number of steps) for each first period (for example, one hour) through clustering or the like of machine learning. Moreover, it is possible to have an effect on presenting a target or health by inputting an external factor of an individual. In the habit improving device in the first aspect, instead of performing judgement simply based on the average value of the activity amounts as in technology in the related art, since the patterns of the activity amounts are grouped, it is possible to find an abnormality in the current distribution pattern through a comparison with a regular pattern and inform the user of the necessity for setting a different target. Moreover, it is also possible to present advice information for setting this target.

In addition, in the habit improving device in the first aspect of the present disclosure, it is possible to acquire a desired distribution pattern, a desired period of the target pattern, and a desired time for advice by changing the first period and the second period. For example, in the case of (the first period and the second period)=(one hour and one day), it is possible to inform of a daily distribution pattern which is variable every hour, and it is possible to provide the advice information every hour. In another example, in the case of (the first period and the second period)=(one day and one month), it is possible to obtain a monthly distribution pattern which is variable every day. For example, in the case of (the first period and the second period)=(one week and one year), it is possible to obtain a yearly distribution pattern which is variable every week. If the first period and the second period are appropriately set in this manner, the user can acquire a desired distribution pattern and a desired target pattern. Moreover, by adjusting these periods, it is possible to adjust an interval at which the user can be provided with the advice information, analyze the distribution patterns corresponding to any of a short term, an intermediate term, and a long term, and provide corresponding advice information to the user.

Moreover, the habit improving device according to the first aspect of the present disclosure need only be a device capable of acquiring activity amount information of the user, the attribute information, and the external factor information, sorting them into groups, generating a target pattern, and executing a program for presenting the advice information. For example, wearable equipment (for example, a smartphone or a wristwatch-type wearable terminal), an activity amount meter, or a stationary device (for example, a personal computer) may be adopted. In addition, for example, the habit improving device in the first aspect of the present disclosure may or may not be worn by the user and need only be able to acquire the activity amount information or the like. For example, the user may wear a detection device capable of detecting an activity amount, and the habit improving device may acquire the activity amount information from this detection device and execute the foregoing program.

In the habit improving device according to a second aspect of the present disclosure, the second calculation unit judges whether the user has deviated from a position scheduled in accordance with a schedule with reference to schedule information relating to the schedule of the user and positional information of the user and changes the target pattern in accordance with a deviated position when it is judged that the user has deviated. The presenting unit presents the advice information based on the current distribution pattern and the changed target pattern.

In the foregoing constitution, the second calculation unit judges whether a current location of the user has deviated from a position scheduled in accordance with the schedule with reference to the schedule information of the user and the positional information of the user. For example, the second calculation unit judges whether a current location of the user is away from a position scheduled in accordance with the schedule information by a distance set in advance or longer. When it is judged it is way therefrom by this distance or longer, the second calculation unit judges that the user has deviated from the scheduled position. When it is judged that the user has deviated from the scheduled position, the second calculation unit changes the target pattern in accordance with the deviated position (a place or a building present at the position thereof linked to the place). For example, when the deviated position is a sports gym, on the assumption that it is an opportunity for increasing the activity amount, a target pattern for raising the activity amount is generated. On the other hand, when the deviated position is a restaurant, the activity amount is further increased than usual in consideration of the time after the meal or a rest at the restaurant. Regarding the time to leave the restaurant, the second calculation unit estimates a leaving time by estimating the meal contents from a time zone at the time of entry to the restaurant, for example. Further, the presenting unit can present appropriate advice information by presenting the advice information to the user based on the current distribution pattern and the changed target pattern.

In the habit improving device according to a third aspect of the present disclosure, the second calculation unit uses at least one of physical information, residence information, occupation, a workplace, hobbies, and favorite food and drink of the user as the attribute information.

In the foregoing constitution, the attribute information used by the second calculation unit is regulated. The attribute information is information used when a target pattern of the user is calculated. Examples thereof include physical information necessary when the activity amount of the user is measured, residence information for being associated with an external factor, information of occupation, a workplace, and the like, information regarding hobbies relating to activities, and information relating to favorite food and drink utilized when eating out. In addition, the attribute information may be utilized by the presenting unit presenting appropriate advice information.

In the habit improving device according to a fourth aspect of the present disclosure, the second calculation unit uses at least one of positional information of the user, weather forecast information based on the positional information, and schedule information relating to a schedule of the user as the external factor information.

In the foregoing constitution, the external factor information used by the second calculation unit is regulated. The external factor information is information used for performing calculation by associating the target pattern that becomes a target for the user with the groups, and the external factor information includes positional information indicating a current location of the user, weather forecast information based on the positional information (for example, weather conditions for every hour from then on), and/or schedule information of the user (for example, a schedule for every hour from then on). Based on the external factor information, the second calculation unit can perform calculation by associating an accurate target pattern with the groups. In addition, positional history information in which history of this location is recorded may be included in addition to the positional information. Easiness of performing activities may be recorded or predicted in accordance with particular places and this may be included in the external factor information. The external factor information may be any information as long as it is an external factor affecting the user, and it is not limited to the matters described herein.

In the habit improving device according to a fifth aspect of the present disclosure, the presenting unit includes a calculation unit which calculates a difference between the current distribution pattern and a target pattern corresponding to the current distribution pattern for each of the first periods, and an advice generation unit which generates the advice information based on the difference.

In the foregoing constitution, the presenting unit acquires the difference between the current distribution pattern and the target pattern corresponding to this distribution pattern, calculates the difference including a sign for each of the first periods that is the smallest unit for totaling the activity amount of the distribution pattern, and calculates how much the current distribution pattern is larger or smaller than the target pattern for each of the first periods based on this difference. Further, the presenting unit generates the advice information to be presented to the user based on this difference for each of the first periods. The advice information is a comment for improving lifestyle habits of the user. For example, since the activity amount based on the distribution pattern until the present is smaller than the target pattern, it is a comment for prompting the user to increase the activity amount from then on. The presenting unit may calculate this activity amount and a time zone thereof based on external factor information of the user as well. In this case, for example, the presenting unit calculates the activity amount and the time zone based on that it is the time zone scheduled for activities of the user in accordance with the schedule, and furthermore, based on whether activities can be performed outside at this time zone by means of a weather forecast when it is the time scheduled for activities, and generates corresponding advice information.

In the habit improving device according to a sixth aspect of the present disclosure, the presenting unit compares the current distribution pattern and a target pattern corresponding to the current distribution pattern and presents the same to the user as the advice information.

In the foregoing constitution, for example, since the presenting unit compares the current distribution pattern and the corresponding target pattern to each other and presents the result to the user, the user can be informed of a part of the pattern which has reached the target, other parts which have not reached the target, and the degree and the time of performing activities from then on. For example, in the distribution pattern, when the activity amount is stated in time history, the target and the performed activity amount can be compared to each other for every unit time measuring the activity amount, and thus the user can easily recognize the activity amount necessary to achieve the target.

In the habit improving device according to a seventh aspect of the present disclosure, the first calculation unit uses at least one of an amount of consumed energy consumed by the user and the number of steps of the user as the activity amount.

In the foregoing constitution, the first calculation unit calculates the activity amount using the amount of consumed energy consumed by the user and/or the number of steps of the user. For this reason, for example, the first calculation unit can measure the amount of consumed energy using the activity amount meter and can also measure the number of steps using a pedometer. For example, the activity amount meter calculates the activity amount by detecting change in movement or posture of a human body and identifying various activities using an acceleration sensor (three-dimensional acceleration sensor) and an air pressure sensor. Activities relate to movement of a human and indicate physical activities, for example, in walking, jogging, cleaning, or laundering. For example, regarding walking, an ordinary speed, a slow speed, a fast walking speed, and the like can also be identified. The amount of consumed energy indicates the total amount of energy consumed by the user during a certain period (for example, one day).

The habit improving device according to an eighth aspect of the present disclosure further includes a pattern generation unit which generates, for each of the groups, one of the distribution patterns belonging to the groups as a model pattern that is a typical pattern of the groups.

In the foregoing constitution, the pattern generation unit generates a pattern typical for a group for each of the groups. In the habit improving device according to the eighth aspect, one of the distribution patterns belonging to the groups is generated as a typical pattern. For this reason, when the groups are handled, a model pattern generated by the pattern generation unit can be used. Since a group can be handled as a pattern, when the second calculation unit performs calculation by associating the target pattern with a group, calculation can be performed based on the model pattern.

In the habit improving device according to a ninth aspect of the present disclosure, the sorting unit sorts a plurality of the distribution patterns into the groups based on a plurality of the model patterns set in advance.

In the foregoing constitution, the sorting unit sorts a plurality of distribution patterns into groups using a model pattern that is set in advance and indicates features of the groups for each of the groups. A characteristic viewpoint in the habit improving device according to this aspect is that a model pattern is set in advance, and a setter such as a user can set a model pattern in advance. Since a model pattern can be set in advance, it is possible to give a significance to a model pattern in advance. In the habit improving device according to the second aspect, similar distribution patterns are gathered, one group is formed, and a significance is given to the features of the groups from the formed group. On the other hand, in the habit improving device according to this aspect, a feature of a group (here, a model pattern) is determined first before a group is formed, a group is set based on this feature, and the distribution patterns are sorted based on this group.

In addition, the technique of this aspect and the technique of a tenth aspect (which will be described below) may be used. For example, the distribution patterns may be grouped by the technique of the tenth aspect, a model pattern of the group which the user considers useful is set for each of the groups based on the group, and grouping may be performed again by the technique of this aspect based on this model pattern. As a result, since a model pattern can be set by this technique based on a distribution of actual distribution patterns by the tenth technique, groups can be sorted better along with the intention of the user than executing sorting simply by each of the techniques.

In the habit improving device according to the tenth aspect of the present disclosure, the sorting unit includes an acquisition unit which acquires a distribution of a plurality of vectors from the plurality of the distribution patterns calculated by the first calculation unit, the vector having an activity amount for each of the first periods as a component, and one vector corresponding to one distribution pattern during the second period for each of the second periods; and a clustering unit which performs sorting by clustering a plurality of points into one or more groups based on positions of the plurality of points within a space laid in a basis determined from the component while the points within the space correspond to the vectors.

In the foregoing constitution, one vector that is a vector having an activity amount for each of the first periods as a component corresponds to one distribution pattern for each of the second periods during the second period. In addition, the points within the space laid in the basis determined from the component correspond to the vectors. For example, the vector indicates a position vector, and a starting point of the position vector corresponds to an origin at which the activity amount is zero in all the first periods included in a certain second period, and an ending point of the position vector corresponds to one distribution pattern. That is, the acquisition unit acquires a distribution of a plurality of vectors from a plurality of distribution patterns calculated by the first calculation unit while one vector corresponds to one distribution pattern for each of the second periods during the second period. A space in which a number equal to or smaller than the number of first periods included in the second period becomes the number of dimensions and each axis indicates the activity amount during the first period is prepared. For example, in the sorting unit, when the first period is one hour and the second period is one day, the maximum number for the first period is 24. Therefore, a space prepared in this case is a 24-dimensional space at the most, and each axis corresponds to the activity amount of the user for every hour from 0:00 to 24:00. That is, a space in this example is a 24-dimensional space including 24 axes at the maximum, such as an axis indicating the activity amount from 0:00 to 1:00, an axis indicating the activity amount from 1:00 to 2:00, and so on to an axis indicating the activity amount from 23:00 to 24:00. In addition, in this example, the space may be a space equal to or smaller than a 24-dimensional space. For example, the space may be a 17-dimensional space realized by dividing a period from 6:00 to 23:00 every hour during which the user is assumed to be active. Moreover, the acquisition unit calculates one point within the space corresponding to the distribution pattern for each of the second periods (for example, one day) and similarly acquires a plurality of points corresponding to a plurality of calculated distribution patterns. For this reason, the acquisition unit can obtain as many points as the number of distribution patterns within the space. The clustering unit performs clustering of the plurality of points into one or more groups based on positions of the points distributed within the space. As a result, the clustering unit can sort the distribution patterns into groups assumed to have a similar distribution tendency.

Therefore, according to the habit improving device in the tenth aspect of the present disclosure, a plurality of distribution patterns can be sorted by causing the activity amount for the second period or smaller for each of the first periods to correspond to one point within the space and sorting the points into groups through clustering of a distribution of the points.

In the habit improving device according to an eleventh aspect of the present disclosure, the clustering unit compares distances between a certain point and other points within the space to each other and performs grouping such that two points at the shortest distance belong to the same group; and compares distances between a point belonging to a certain group and a plurality of points belonging to other groups and performs grouping of groups of the points at the shortest distance as the same group when the shortest distance of the distances is equal to or smaller than a threshold.

In the foregoing constitution, the clustering unit performs grouping of a plurality of points by obtaining distances between points distributed within the space (which is generally a multi-dimensional space) and comparing the distances to each other. It is desirable that the distances within the space used in the present embodiment satisfy an axiom for a mathematical distance. However, the axiom for a mathematical distance is not a necessary and sufficient condition for the distances in the present embodiment. More specifically, the axiom for a distance is a necessary and sufficient condition for a mathematical distance but is not a necessary condition for the concept of a distance in the embodiment of this application. In addition, distances herein are established by extending the concept of a distance in a one-dimensional space, a two-dimensional space, or a three-dimensional space, and there may be various definitions. Among the definitions for these distances, typical examples thereof include a Euclidean distance, a city block distance, a Minkowski distance, a Mahalanobis distance, and cosine similarity (a concept opposite to that of a distance). A distance may also be referred to as dissimilarity, which is a function for measuring sizes of comparison objects in data or a cluster. In the present disclosure, any of the distances, the dissimilarity, and/or the similarity may be used. However, in the description herein, for the sake of convenience, they will be stated as distances, and all the concepts described herein are included therein.

In addition, in the habit improving device according to the eleventh aspect, a specific example that is a model executed by the clustering unit is described. However, there are various other techniques (aggregation-type (or division-type) hierarchical clustering, optimization clustering, and the like). For example, a technique of aggregation-type hierarchical clustering may be executed by the following procedure, for example. First, the procedure starts on the assumption that each of the points forms an isolated group. In all of these groups, distances between pairs of groups are calculated to find a pair of groups at the shortest distance. Further, a new group is generated by merging this pair of groups, and distances between this new group and other groups are calculated. Next, in the pairs of groups including this new group, another new group is generated by finding a pair of groups at the shortest distance and combining this pair of groups. Hereinafter, similarly, combining of groups and recalculation of distances are repeated, and the processing proceeds until the time when all the points are in one group. Then, the processing returns to the groups at the time of an appropriate number of groups, an appropriate number of times of combining, or the like, and the number of groups is decided. The clustering unit can proceed grouping and divide a plurality of points into groups based on the distances (dissimilarity) in accordance with the procedure described above.

In the habit improving device according to a twelfth aspect of the present disclosure, the sorting unit performs sorting into the groups based on whether an activity amount of the distribution pattern in a particular time zone is equal to or larger than a threshold.

In the foregoing constitution, the distribution patterns are sorted into groups based on whether the activity amount in a particular time zone in the distribution pattern of the activity amount is large (that is, whether it is equal to or larger than the threshold). In this technique according to the twelfth aspect, for example, when the activity amount after 0:00 at late night (for example, before 2:00) is large, when the activity amount before 6:00 in the early morning (for example, after 4:00) is large, and/or when the activity amount during the daytime (for example, from 9:00 to 15:00) is small (smaller than a certain threshold), the sorting unit respectively sorts the distribution patterns into corresponding groups. Similar to the habit improving device according to the ninth aspect, a characteristic viewpoint for the habit improving device according to the twelfth aspect is that a model pattern is set in advance and a setter such as a user can set features of the groups in advance. In the habit improving device according to the twelfth aspect, since a model pattern can be set in advance, it is possible to give a significance to the model pattern in advance.

The habit improving device according to another aspect further includes a pattern generation unit which generates a distribution pattern corresponding to points determined based on a distribution of points belonging to the groups as a model pattern that is a typical pattern of the groups.

In the foregoing constitution, the pattern generation unit generates a pattern typical for a group for each of the groups based on a distribution of points within the space. In the habit improving device according to this aspect, a distribution pattern corresponding to a point, of the points indicating a distribution pattern belonging to the group, determined based on a distribution within the group is generated as a typical pattern. Examples of a point, of the points indicating a distribution pattern belonging to the group, determined based on a distribution within the group include the center of gravity determined based on a plurality of points within a group and the center of a space in which groups are distributed. For this reason, when the groups are handled, a model pattern generated by the pattern generation unit can be used. Since a group can be handled as a pattern, when the second calculation unit performs calculation by associating the target pattern with a group, calculation can be performed based on the model pattern.

In the habit improving device according to another aspect, the sorting unit includes an acquisition unit which calculates one point corresponding to one of the distribution patterns within the space for each of the second periods including the first period and acquires a distribution of a plurality of vectors from the plurality of the distribution patterns calculated by the first calculation unit, the vector having an activity amount for each of the first periods as a component, and one vector corresponding to one distribution pattern during the second period for each of the second periods; and a clustering unit which performs sorting by clustering a plurality of points into one or more groups based on positions of the plurality of points within a space laid in a basis determined from the component while the points within the space correspond to the vectors. The space is a space constituted of axes corresponding to the first periods having an amount indicated by a certain index of the activity amounts and axes corresponding to the first periods having an amount indicated by another index of the activity amounts.

In the foregoing constitution, since the acquisition unit has axes corresponding to the first periods having an amount indicated by a certain index of the activity amounts and axes corresponding to the first periods having an amount indicated by another index of the activity amounts, twice the number of first periods included in the second period becomes the maximum number of dimensions. For example, a certain index of the activity amounts is the number of steps, and another index of the activity amounts is the amount of consumed energy. In this example, when the first period is one hour and the second period is one day, the space is a 48-dimensional space at the maximum. A space in which axes indicate a certain index and another index of the activity amounts during the first period is prepared. For example, in the sorting unit, when the first period is one hour and the second period is one day, the maximum number for the first period is 24. Therefore, since a space prepared in this case has two kinds of indices (that is, two kinds including "a certain index" and "another index" described above), it is a 48-dimensional space at the maximum, and each axis corresponds to the activity amount of the user for every hour from 0:00 to 24:00 for each of the indices. That is, a space in this example is a 48-dimensional space including 2×24 axes at the maximum, such as two axes indicating the activity amount from 0:00 to 1:00, two axes indicating the activity amount from 1:00 to 2:00, and so on to two axes indicating the activity amount from 23:00 to 24:00. In addition, in this example, the space may be a space equal to smaller than a 48-dimensional space. For example, the space may be a 34-dimensional space realized by dividing a period from 6:00 to 23:00 every hour during which the user is assumed to be active.

Moreover, the acquisition unit calculates one point within the space corresponding to the distribution pattern for each of the second periods (for example, one day) and similarly acquires a plurality of points corresponding to a plurality of calculated distribution patterns. For this reason, the acquisition unit can obtain as many points as the number of distribution patterns within the space. The clustering unit performs clustering of the plurality of points into one or more groups based on positions of the points distributed within the space. As a result, the clustering unit can sort the distribution patterns into groups assumed to have a similar distribution tendency. In addition, according to this habit improving device, since activity amounts of different kinds are used as axes, there is a probability that the features of the groups can be more noticeable.

In addition, a different kind of the activity amount corresponding to an axis of the space may be selected and it does not have be a particular kind. Examples of the kind of the activity amount include activity energy, basal metabolism, diet-induced thermogenesis, the number of fast steps, and the number of stair-climb in addition to those described above.

Advantageous Effects of Invention

According to the present invention, in an aspect, it is possible to provide a habit improving device, a method, and a program in order to take into account both the user's activity amount and factors other than activity amount to guide the user to have suitable lifestyle habits.

BRIEF DESCRIPTION OF DRAWINGS

FIG. 5 is a flowchart schematically showing an example of a processing procedure relating to the habit improving device according to the embodiment.

FIG. 6A is a flowchart schematically showing an example of the processing procedure of Step S502 in FIG. 5.

FIG. 6B is a table showing an example of activity amount information obtained through the processing procedure in FIG. 6A.

DESCRIPTION OF EMBODIMENT

Hereinafter, an embodiment according to an aspect of the present invention (which will hereinafter be stated as "the present embodiment") will be described based on the drawings. In the following embodiment, parts having the same number are considered to perform similar operation, and therefore duplicate description thereof will be omitted.

[Overview]

Figure 1:
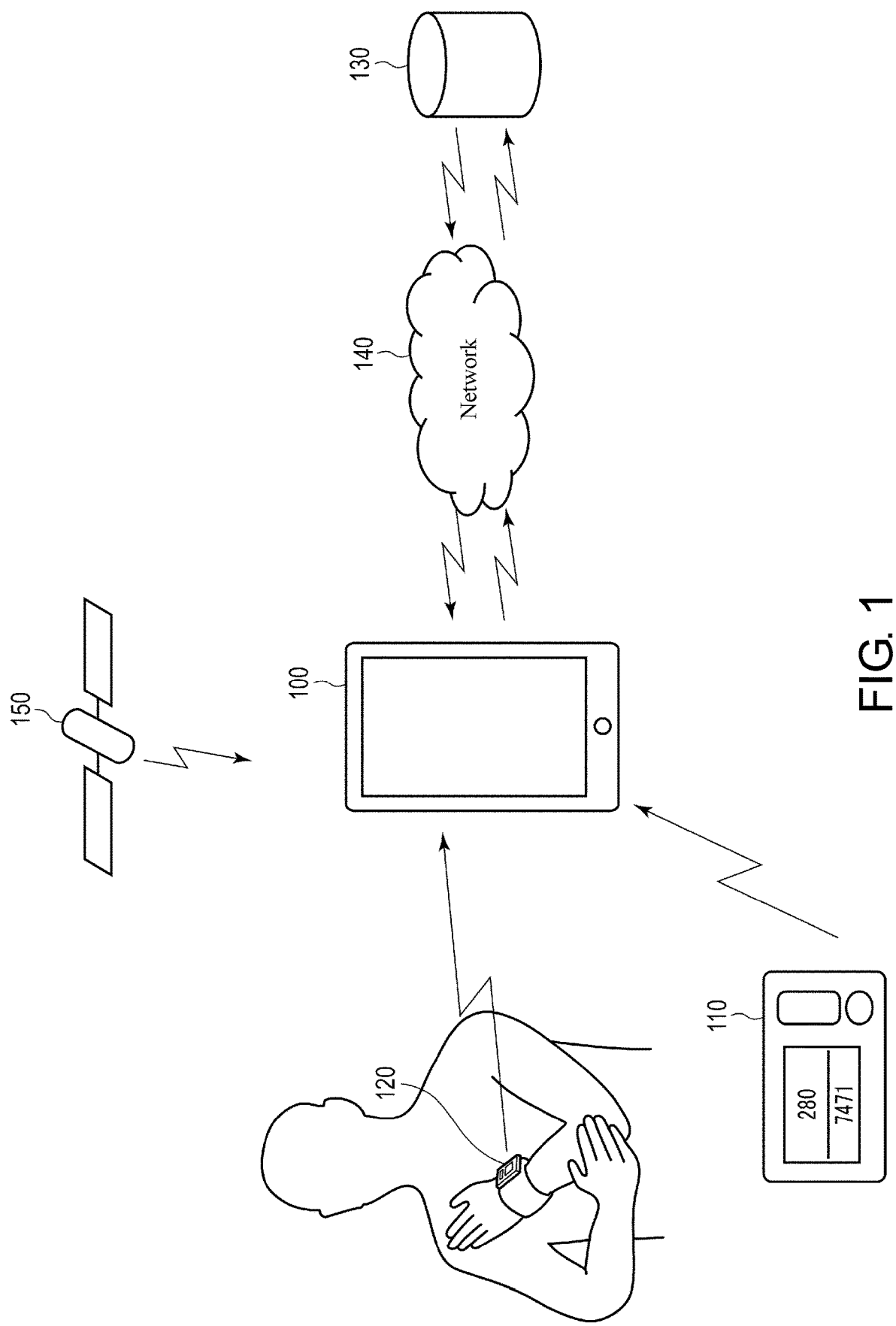
FIG. 1 is a view illustrating an overview of a system including a habit improving device according to an embodiment, an activity amount meter, a wristwatch-type wearable terminal, and a server connected via a network.

First, using FIG. 1, an overview of a habit improving device of the present invention will be described. FIG. 1 schematically illustrates a habit improving device 100 according to an example of the overview, an activity amount meter 110, a wristwatch-type wearable terminal 120, a server 130, a network 140, and a GPS satellite 150, as an example. The activity amount meter 110 measures an activity amount of a user while it is carried (or worn) by the user. For example, it calculates the activity amount by detecting change in movement or posture of a human body and identifying various activities of the user using an acceleration sensor and/or an air pressure sensor.

The activity amount is an amount of consumed energy, that is, the sum of energy consumed by the user during a certain period (for example, one day). The amount of consumed energy corresponds to the total energy consumption of the user during a certain period and is indicated by the sum of activity energy, basal metabolism, and diet-induced thermogenesis, for example. Activity energy is energy consumed through physical activities or exercise performed by the user. Basal metabolism is energy necessary for maintenance of life (maintaining the body temperature, moving the heart, and the like) and is energy consumed even if the user does not move his/her body. In addition, diet-induced thermogenesis is energy consumed due to activities of digestion, absorption, or the like of food after meals. For example, activity energy is calculated based on the product of a METs value, a weight, an exercise time, and a constant. A METs value is a value indicating a multiple of the amount of consumed energy through exercise with respect to that during rest and is indicated in units of METs. In addition, the METs value is determined by being subdivided for each of exercise and activities.

However, here, the activity amount may be defined as any one or more of activity energy, basal metabolism, and diet-induced thermogenesis and may adopt only activity energy or only activity energy and basal metabolism, for example. Moreover, since good approximation is achieved even if only the number of steps is adopted simply as the activity amount, the activity amount may be the number of steps.

The activity amount meter 110 measures any one or more of the amount of consumed energy or activity energy, basal metabolism, and diet-induced thermogenesis. However, for example, it may measure the number of steps, the number of fast steps, the number of steps during slow walking, or the number of steps of stair-climb or may simply measure only the number of steps. The wristwatch-type wearable terminal 120 can also measure an activity amount similar to that of the activity amount meter 110.

In addition, the habit improving device 100 totals a distribution pattern of the user for each of first periods (for example, one hour) and calculates a distribution pattern throughout a second period (for example, one day) larger than this period based on the activity amount acquired from the activity amount meter 110 and/or the wristwatch-type wearable terminal 120. Further, the habit improving device 100 sorts the calculated distribution pattern into a plurality of groups. Examples of a technique of sorting of groups include clustering and hierarchy sorting, but any technique can be adopted as long as grouping can be performed. After grouping is performed, the habit improving device 100 calculates a target pattern that becomes a target of the user for each of the groups based on attribute information of the user and external factor information on the user. Further, the habit improving device 100 generates advice information for the user by comparing the target pattern and a current distribution pattern to each other and presents the result to a user.

A distribution pattern is expressed as a pattern distributed in a two-dimensional space in which the horizontal axis indicates time and the vertical axis indicates activity amount. For example, the number of degrees indicating, for each of the first periods, the sum total of the activity amount within this period is associated with the time and is displayed in the two-dimensional space by the second period.

Regarding a specific example, a distribution pattern is a pattern in which the sum total amount (every hour) of the activity amount measured during a period from when the user has woken up to bedtime is expressed with one bar graph and as many bar graphs as the wake-up periods are arranged. That is, a distribution pattern need only express change over time of the sum total of the activity amount for each certain period.

A program executed by the habit improving device 100 in order to calculate the target pattern for each of the groups and present the advice information by calculating the distribution pattern and grouping the distribution pattern is acquired from the server 130 providing this program via the network 140, for example. The attribute information of the user may also be acquired from the server 130 having corresponding attribute information via the network 140, and the user may input the attribute information using an input unit of the habit improving device 100. This program may also be naturally stored in the habit improving device 100 in advance. In addition, external factor information is information other than information relating to the user himself/herself and is information relating to an external factor that is a factor affecting the user. Examples thereof include positional information, weather information, and schedule information of the user. The habit improving device 100 also acquires the external factor information from the server 130 via the network 140. The positional information of the user is calculated when the habit improving device 100 receives a signal from the GPS satellite 150, but the habit improving device 100 may receive information from a base station and/or a wireless LAN access point and the positional information may be corrected in accordance with this information.

When the activity amount detected by the activity amount meter 110 and/or the wristwatch-type wearable terminal 120 can be detected by the habit improving device 100 alone, the activity amount detected by the habit improving device 100 may be used without using the activity amount meter 110 or the like. In this case, the habit improving device 100 includes a device part for calculating the activity amount of the activity amount meter 110 and/or the wristwatch-type wearable terminal 120. For example, since the habit improving device 100 is a wearable terminal device (for example, a smartphone), it generally includes an acceleration sensor and a pressure sensor so that the number of steps and the number of stairs can be measured, and thus the activity amount based on the number of steps and the number of stairs can be calculated.

As described above, according to the habit improving device of the present embodiment, the user can be informed of advice for coming closer to having ideal activity habits (for example, walking habits) also taking the external factor into account, and it is expected that the user easily behaves such that activity habits are executed. In addition, according to this habit improving device, a more detailed target pattern for each of the first periods for an individual can be calculated by sorting the activity amounts for each of the first periods through clustering or the like. In addition, it is possible to have an effect on presenting a target or health by taking an external factor with respect to the user into account. Moreover, instead of performing judgement simply based on only the average value of the activity amounts as in technology in the related art, since the pattern of the activity amount is grouped, the habit improving device of the present embodiment can find an abnormality in the current distribution pattern compared to a regular pattern, can inform the user of necessity of a different target setting, and can also present the advice information for setting this target.

[Example of Constitution]
(Constitution of Hardware)
<Habit Improving Device>

Next, using FIG. 2, an example of a constitution of hardware of the habit improving device 100 according to the present embodiment will be described.

Figure 2:
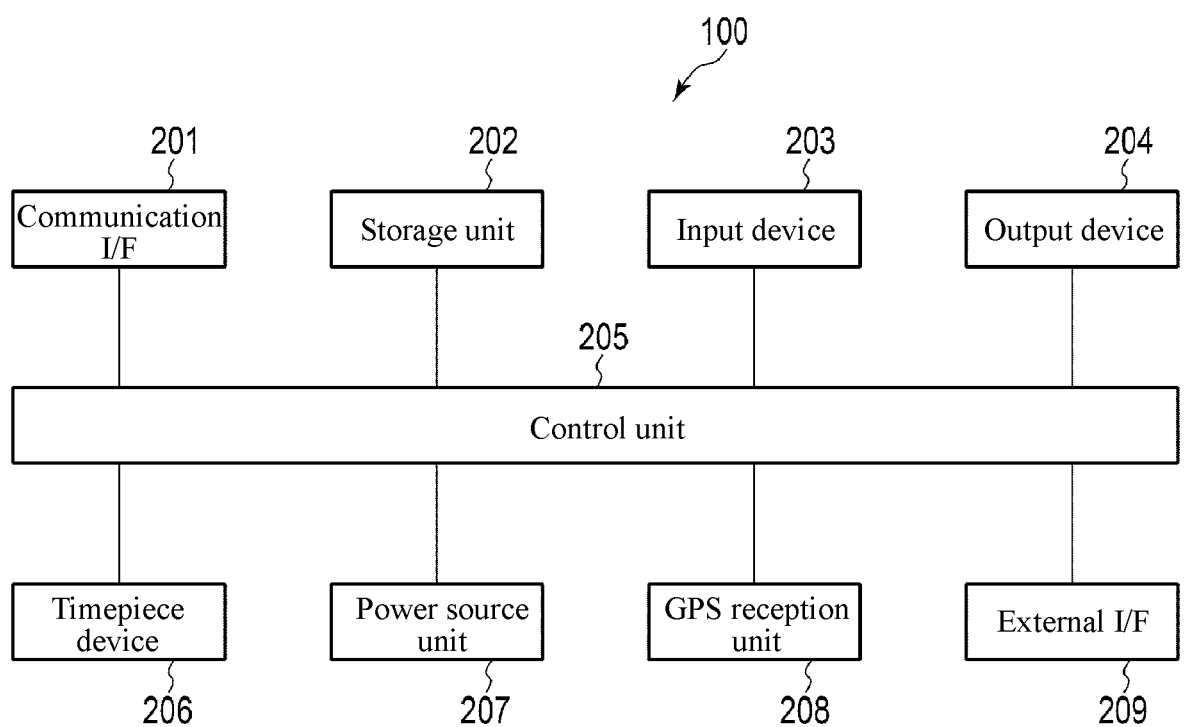
FIG. 2 is a view schematically illustrating an example of a constitution of hardware of the habit improving device according to the embodiment.

As illustrated in FIG. 2, the habit improving device 100 according to the present embodiment includes a computer in which a communication interface 201, a storage unit 202, an input device 203, an output device 204, a control unit 205, a timepiece device 206, a power source unit 207, a GPS reception unit 208, and an external interface 209 are electrically connected to each other. The habit improving device 100 according to the present embodiment corresponds to "the habit improving device" of the present invention. In FIG. 2, the communication interface and the external interface are stated as "a communication I/F" and "an external I/F", respectively.

For example, the communication interface 201 is a short-range wireless communication (for example, Bluetooth (registered trademark)) module, a wired local area network (LAN) module, a wireless LAN module, or the like and is an interface for performing wired communication or wireless communication via a network. The communication interface 201 is an interface for connecting the habit improving device 100 to an external device (for example, a computer or communication equipment on a network). The communication interface 201 is controlled by the control unit 205 to receive activity amount information from the activity amount meter 110 and/or the wristwatch-type wearable terminal 120. Furthermore, the external factor information, the attribute information of the user, and/or the program executed by the habit improving device 100 are downloaded from the server 130 or the like via the network 140.

Communication via this network may be either wireless communication or wired communication. The communication interface 201 may be able to transmit information to an external device via a network. A network may be an inter-network including the Internet, may be a network of other kinds such as an in-hospital LAN, or may be one-to-one communication using a universal serial bus (USB) cable or the like. The communication interface 201 may include a micro-USB connector.

The storage unit 202 is a medium for storing information such as a recorded program due to electrical action, magnetic action, optical action, mechanical action, or chemical action such that a computer, other devices, a machine, or the like can read information such as the program. For example, the storage unit 202 is an auxiliary storage device such as a hard disk drive, a solid-state drive, or the like and stores the activity amount information acquired from the activity amount meter 110 and/or the wristwatch-type wearable terminal 120, pattern information (for example, distribution pattern information and target pattern information) calculated by the control unit 205, the attribute information of the user input from the input device 203 or acquired via the network 140, the external factor information of the user acquired via the network 140, and/or a lifestyle habits improvement presenting execution program executed by the control unit 205 for presenting information for improvement in lifestyle habits to the user based on the acquired activity amount information. Regarding the activity amount information acquired by the activity amount meter 110 or the like, all the activity information from a certain time in the past may be stored in the storage unit 202. In addition, the storage unit 202 may also store group information relating to sorted groups obtained from the distribution pattern. Moreover, the advice information may be stored by being associated with a difference pattern calculated by the execution program. This advice information and the difference pattern may be associated with each other in a table.

The input device 203 is a device for receiving an input, and examples thereof include a touch panel, a physical button, a mouse, and a keyboard. The output device 204 is a device for performing outputting and outputs information by display, audio, or the like. Examples thereof include a display and a speaker.

The control unit 205 includes a central processing unit (CPU), a random access memory (RAM), a read-only memory (ROM), and the like and controls each of the constituent elements in accordance with information processing. The execution program for presenting improvement of lifestyle habits to the user based on the acquired activity amount information is stored in the storage unit 202, and the control unit 205 reads out the execution program from the storage unit 202 and executes processing. In addition, the control unit 205 performs distance measurement computation based on a GPS signal received via the GPS reception unit 208 (which will be described below) and calculates current positional information of the habit improving device 100, that is, a position of a person to be measured (user) wearing the activity amount meter 110 or the wristwatch-type wearable terminal 120.

The timepiece device 206 is a device for measuring a time and can measure the date and the time. For example, the timepiece device 206 is a timepiece including a calendar and gives information of current year and month and/or date and time to the control unit 205.

The power source unit 207 may be anything as long as it can supply electricity. Examples thereof include a rechargeable secondary battery or an AC power source which can be acquired from an ordinary power outlet. The power source unit 207 supplies electricity to each of the elements mounted in a main body of the habit improving device 100. For example, the power source unit 207 supplies electricity to the communication interface 201, the storage unit 202, the input device 203, the output device 204, the control unit 205, the timepiece device 206, the GPS reception unit 208, and the external interface 209.

The GPS reception unit 208 receives GPS signals respectively transmitted from a plurality of GPS satellites and outputs received GPS signals to the control unit 205. The GPS reception unit 208 may be included in the activity amount meter 110 and/or the wristwatch-type wearable terminal 120 instead of the habit improving device 100. These may acquire a GPS signal, the habit improving device 100 may receive a GPS signal via the communication interface 201, and the control unit 205 may calculate the positional information. In addition, the activity amount meter 110 and/or the wristwatch-type wearable terminal 120 may receive a GPS signal, calculate the positional information, and transmit the positional information to the habit improving device 100.

The external interface 209 is an interface for mediating between the main body of the habit improving device 100 and outside. For example, it is a USB port or the like and is an interface for connection to an external device (for example, a memory or communication equipment). For example, the external interface 209 is an interface for connection to an external device such as an acceleration sensor, a gyro-sensor, and/or a magnetic field sensor.

(Constitution of Software)
<Presenting Lifestyle Habits Improvement Plan of Habit Improving Device 100>

Figure 3:
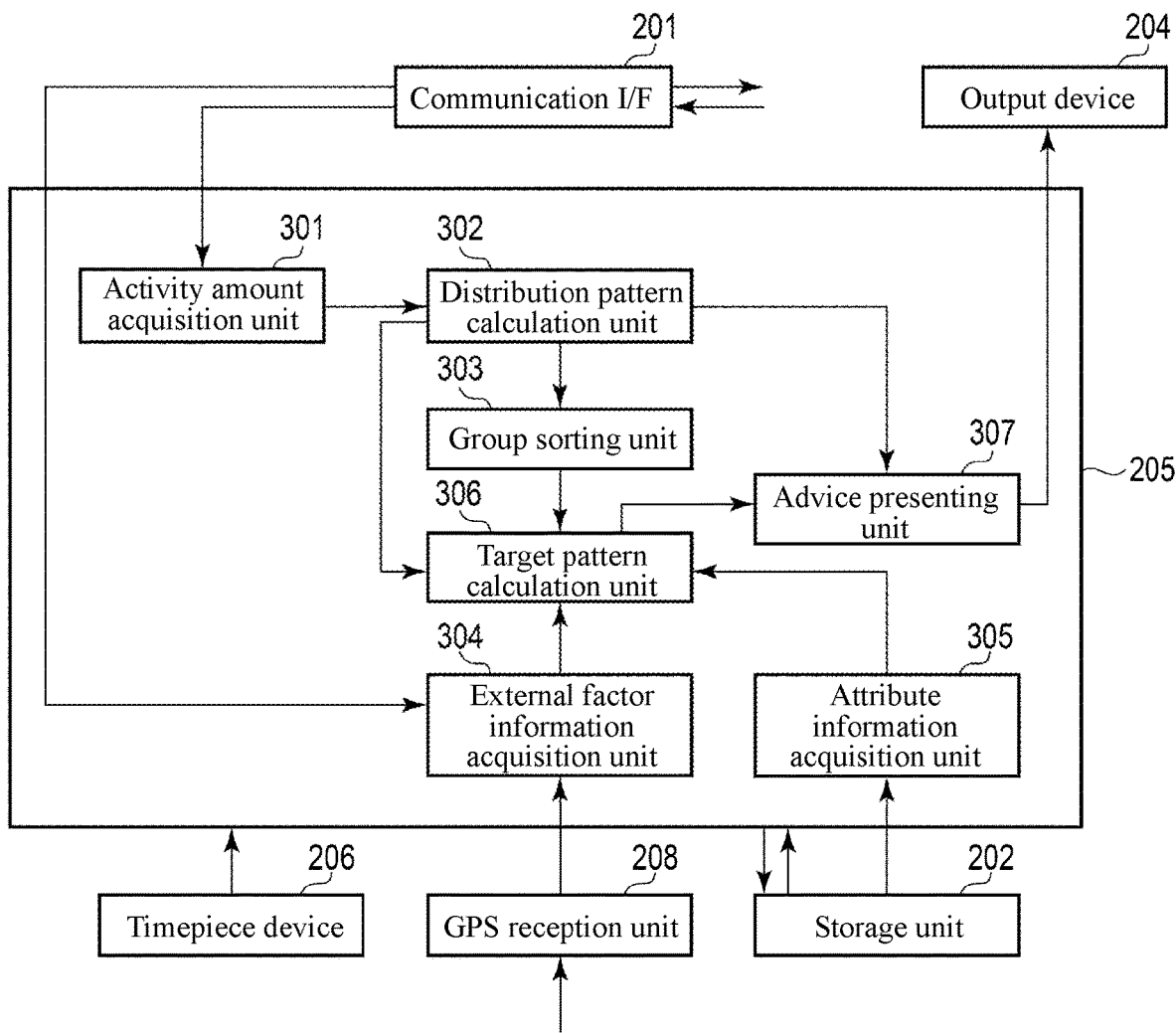
FIG. 3 is a view illustrating an example of a portion of a constitution of software of the habit improving device according to the embodiment.

Next, using FIG. 3, an example of a constitution of software of the habit improving device 100 according to the present embodiment will be described. FIG. 3 illustrates a constitution of software executed by the control unit 205 of the habit improving device 100 for sorting the distribution pattern calculated based on the activity amount of the user into groups, calculating the target pattern for each of the groups, and executing a program for presenting the advice information to the user based on the target pattern and the current distribution pattern.

When a necessary program is executed, the control unit 205 of the habit improving device 100 deploys the execution program stored in the storage unit 202 for presenting the advice information relating to improvement in lifestyle habits to the user in the RAM based on the acquired activity amount information. Further, the control unit 205 controls each of the constituent elements by interpreting and executing the execution program deployed in the RAM for presenting the advice information relating to improvement in lifestyle habits to the user using the CPU. In this manner, as illustrated in FIG. 3, the habit improving device 100 according to the present embodiment includes an activity amount acquisition unit 301, a distribution pattern calculation unit 302, a group sorting unit 303, an external factor information acquisition unit 304, an attribute information acquisition unit 305, a target pattern calculation unit 306, and an advice presenting unit 307.

The activity amount acquisition unit 301 acquires desired activity amount information of the user from the external activity amount meter 110 or the like via the communication interface 201. The activity amount acquisition unit 301 acquires the activity amount information acquired by an external activity amount sensor via the communication interface 201 for each of certain periods. For example, a certain period is every hour. However, the activity amount acquisition unit 301 may acquire the activity amount information by a shorter period, such as every minute or the like. In addition, the external activity amount sensor is the activity amount meter 110, the wristwatch-type wearable terminal 120, or the like. However, the habit improving device 100 may include these devices, and the activity amount acquisition unit 301 may acquire the activity amount information from these devices.

The distribution pattern calculation unit 302 totals (aggregates) the activity amount acquired by the activity amount acquisition unit 301 for each of the first periods and calculates the distribution pattern in which the first periods are united to form the second period. Hereinafter, a case in which the first period is one hour and the second period is one day will be described as a main example. When the activity amount is the number of steps, the activity amount acquisition unit 301 calculates the sum of the number of steps made by the user every hour in the time zone thereof. For example, the distribution pattern calculation unit 302 calculates this number of steps as much as 24 hours and obtains bar graphs having the horizontal axis as time and the vertical axis as number of steps. In this example, the distribution pattern calculation unit 302 obtains as many bar graphs as the number of steps for 24 (including zero steps) corresponding to the time zone as a distribution pattern for one day. The distribution pattern calculation unit 302 calculates the distribution pattern for a plurality of second periods and obtains a plurality of distribution patterns. For example, the distribution pattern calculation unit 302 calculates the distribution pattern for every day. However, when activity amount information in the past is present in the storage unit 202 at the time when the habit improving device 100 has started, the distribution pattern calculation unit 302 may go back to the past and calculate the distribution pattern until the present or may calculate the distribution pattern for each of the first periods.

The group sorting unit 303 sorts a plurality of distribution patterns calculated by the distribution pattern calculation unit 302 into one or more groups. The group sorting unit 303 sorts the groups such that a different group has a different feature. Regarding a technique of performing sorting, the group sorting unit 303 can adopt clustering, hierarchy sorting, or the like, and a technique of performing sorting is not particularly limited. A more specific example will be described below with reference to FIGS. 7A, 7B, and 7C.

When the group sorting unit 303 sorts the groups through clustering, for example, a 24-dimensional space having 24 axes as axes indicating the number of steps for every hour is prepared. The group sorting unit 303 sorts the groups using a space in which the axes correspond to the number of steps of the user for every hour from 0:00 to 24:00. Moreover, the group sorting unit 303 calculates a position of one point within the space corresponding to the distribution pattern for every day and similarly calculates positions of a plurality of points corresponding to a plurality of calculated distribution patterns. For this reason, the distribution pattern calculation unit 302 obtains as many points as the number of distribution patterns within the space. The group sorting unit 303 performs clustering of the plurality of points into one or more groups based on the positions of the points distributed within the space. As a result, a clustering unit can sort the distribution pattern into groups assumed to have a similar distribution tendency. In addition, regarding another expression, a vector having the number of steps of the user for every hour as a component may be considered, and the points within the space laid in a basis determined from the component may correspond to this vector. For example, this vector indicates a position vector, and a starting point of the position vector corresponds to an origin at which the number of steps is zero in all the periods for every hour included in one day, and an ending point of the position vector corresponds to one distribution pattern.

When the group sorting unit 303 sorts the groups through hierarchy sorting, for example, the group sorting unit 303 sorts the groups based on whether the activity amount in a particular time zone is equal to or larger than a threshold. As an example, sorting of two groups is performed whether the activity amount is equal to or larger than the threshold in a time zone from 23:00 at late night until 2:00 before dawn of the next day. The threshold is provided for each of a plurality of time zones, the groups are divided whether the activity amount is equal to or larger than the threshold, and a plurality of groups is generated. Furthermore, the group sorting unit 303 may provide a plurality of thresholds for the same time zone, and grouping may be performed for three or more groups at this time zone based on the threshold. For example, the group sorting unit 303 performs sorting of three groups such as a group of steps fewer than 500 steps during a period from 10 a.m. to 12 a.m., a group of steps within a range of 500 steps to fewer than 1,000 steps, and a group of steps more than 1,000 steps. In this case, there are two thresholds for 500 steps and 1,000 steps.

The external factor information acquisition unit 304 acquires the external factor information relating to an external factor that is not directly related to the user, is information other than the attribute information of the user, and is a factor affecting the user from the network 140 or the like via the communication interface 201. Examples of the external factor information include positional information indicating a current location of the user, the weather forecast information based on the positional information (for example, weather conditions for every hour from then on), and schedule information of the user (for example, a schedule for every hour from then on). In the present embodiment, this external factor information is information used for performing calculation by associating the target pattern that becomes a target for the user with the groups. In addition, positional history information in which history of this location is recorded may be included in addition to the positional information. Easiness of performing activities may be recorded or predicted in accordance with particular places and this may be included in the external factor information. The external factor information may be any information as long as it is an external factor affecting the user, and it is not limited to the matters described herein. In addition, the external factor information may be utilized for the advice presenting unit 307 to present appropriate advice information.

The attribute information acquisition unit 305 acquires the attribute information that is information relating to an attribute of the user from the storage unit 202. In addition, the attribute information is information used when a target pattern of the user is calculated. Examples thereof include physical information (for example, a gender, a height, and a weight) necessary when the activity amount of the user is measured, residence information for being associated with an external factor, occupation information such as occupation and a workplace, information regarding hobbies relating to activities, and information relating to favorite food and drink utilized when eating out. In addition, the attribute information may be utilized by the advice presenting unit 307 presenting appropriate advice information.

The target pattern calculation unit 306 calculates the target pattern that becomes a target of the user based on the attribute information and the external factor information for each of the groups sorted by the group sorting unit 303. The target pattern calculation unit 306 calculates a target pattern desirable for the user in accordance with the attribute information of the user and an external factor affecting the user while indirectly reflecting the features of the groups. Moreover, the target pattern calculation unit 306 may calculate a target pattern from then on with reference to the distribution pattern which is currently in progress and is not completed yet and/or the distribution pattern before the preceding day, and the target pattern (and/or the advice information).

The advice presenting unit 307 generates the advice information for the user and gives it to the output device 204 based on the distribution pattern which is acquired from the distribution pattern calculation unit 302 and is currently in progress, and the target pattern corresponding to the distribution pattern currently in progress of the target pattern calculated for each of the groups by the target pattern calculation unit 306. The advice information is generated every time a target pattern is calculated and is generated every time a target pattern is changed. In addition, the latest advice information may be stored in the storage unit 202 at all times such that the advice information can be presented to the user based on the target pattern which is effective at that time when the user performs a predetermined operation. When the advice information is received from the advice presenting unit 307, the output device 204 presents this information to the user. A pattern which is being currently acquired has a content corresponding to the target pattern, and each of the first period and the second period in which the distribution pattern is acquired has the same length as the target pattern, and the kind of the activity amount is also the same as each other. Examples of the kind of the activity amount include the amount of consumed energy, activity energy, and the number of steps. The advice presenting unit 307 stores the distribution pattern and the target pattern during the second period in the storage unit 202 as history information. Moreover, the advice presenting unit 307 may also store the advice information in the storage unit 202 in association with the distribution pattern and the target pattern. In addition, the difference pattern of the distribution pattern and the target pattern and the advice information may be stored in the storage unit 202 in association with each other (for example, as a table).

<Others>

Operation of the habit improving device 100 will be described in detail in an operational example which will be described below. In the present embodiment, all the control units 205 of the habit improving device 100 may be realized by a general-purpose CPU. However, a portion or all of the foregoing operation (or functions) may be realized by one or a plurality of dedicated processors. In addition, regarding a constitution of the habit improving device 100, omission, replacement, and addition may be suitably performed in accordance with the embodiment.

Figure 4:
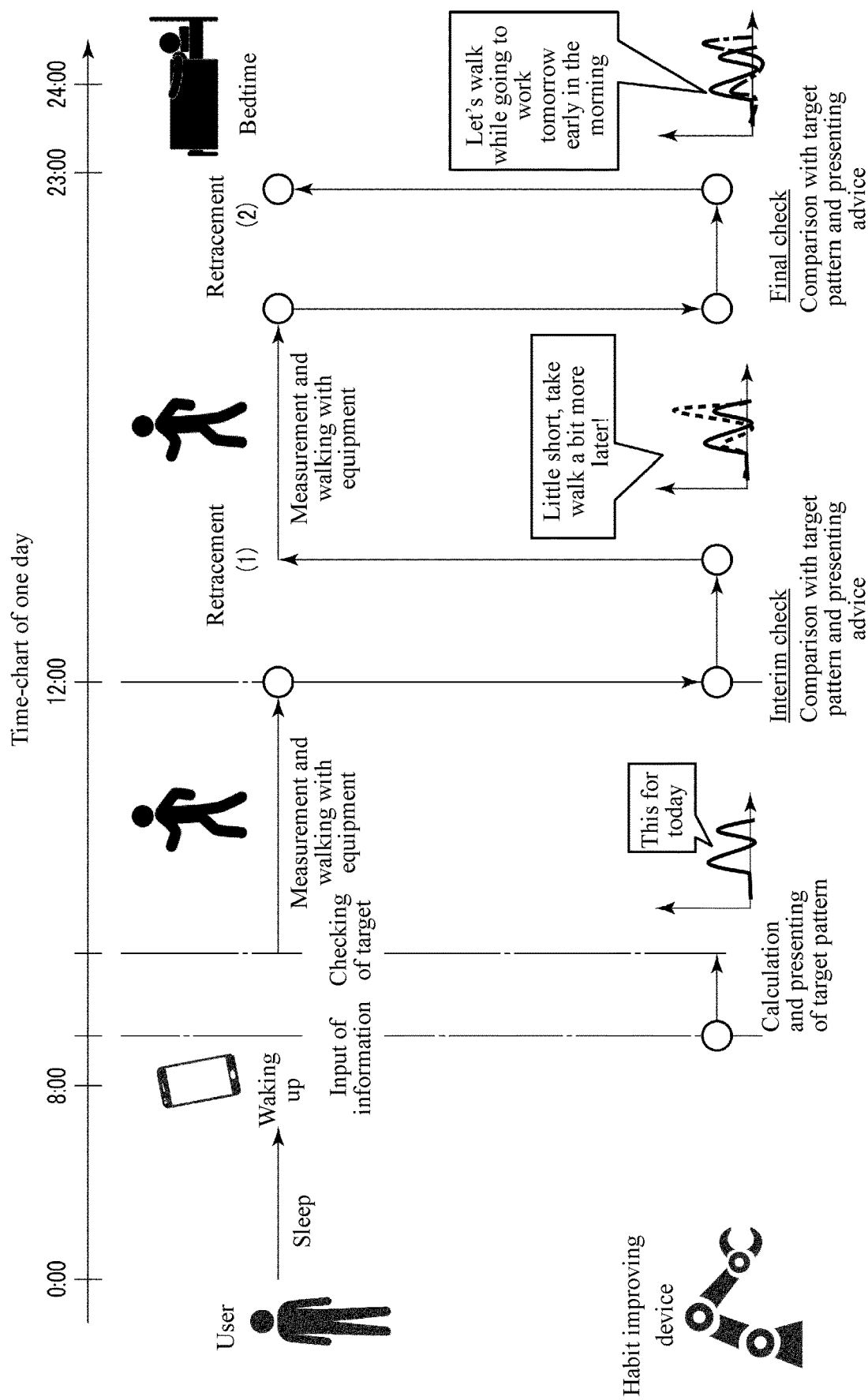
FIG. 4 is a time-chart of one day illustrating operation of the habit improving device according to the embodiment and behavior of a user.

Next, using FIG. 4, an example of behavior of the user in one day when the habit improving device 100 is used, and the advice information of the habit improving device 100 will be displayed and described. FIG. 4 is a time-chart schematically showing an example of behavior of the user in one day and an example of operation and display of the habit improving device 100.

(0:00 a.m.) The user is scheduled to go to bed before 0:00 a.m. and wake up at 8:00 a.m. The user wears the activity amount meter 110 and/or the wristwatch-type wearable terminal 120 during sleep so that this equipment detects the activity amount, and the activity amount acquisition unit 301 of the habit improving device 100 acquires this activity amount information. In addition, the activity amount meter 110 and the wristwatch-type wearable terminal 120 may be turned off so that the user may not wear these at the time of sleeping, and the habit improving device 100 may also be turned off.

(8:00 a.m.; waking up in the morning) The user wakes up at 8:00 a.m. Thereafter, the user inputs the attribute information of the user, the external factor information, the schedule information, and the like to the habit improving device 100 using the input device 203. However, in the foregoing information, information which can be acquired in advance (for example, the attribute information of the user and the schedule information) may be stored in the storage unit 202 of the habit improving device 100 in advance by the user. In addition, after the user has woken up, the output device 204 of the habit improving device 100 displays a daily target pattern of today for the user. The target pattern is calculated by the control unit 205 of the habit improving device 100 based on the activity amount before waking up in the morning. Particularly, when there is the advice information associated with the target pattern, the output device 204 displays the advice information. In the example of FIG. 4, the target pattern is displayed together with a wording of "this for today". Naturally, a wording may be output by the output device 204 in audio. In addition, immediately after waking up or after a while, the advice information may be presented to the user in display or audio such that the user wears the activity amount meter 110 and/or the wristwatch-type wearable terminal 120. Thereafter, the user wears the activity amount meter 110 or the like, checks the target pattern, and starts behavior of a day.

(12:00 a.m.; interim check) The habit improving device 100 calculates the target pattern. Moreover, it generates advice information based on the distribution pattern indicating the activity amount in the morning and the target pattern (retracement (1)). The output device 204 displays the target pattern and the distribution pattern in the morning, and the advice information is also presented to the user by the output device 204 in audio or an image. In the example of FIG. 4, since the activity amount in the morning is smaller than the activity amount based on the target pattern, the output device 204 presents advice information such as "a little short, take a walk a bit more later!" to the user. Furthermore, the habit improving device 100 presents the distribution pattern together with the target pattern to the user utilizing the output device 204.

(23:00 p.m.; final check) Similar to the interim check, the habit improving device 100 calculates the target pattern. Moreover, it generates the advice information based on a daily distribution pattern and a daily target pattern of today (retracement (2)). The output device 204 displays the distribution pattern indicating the target pattern of today and the activity amount of today, and the advice information is also presented to the user by the output device 204 in audio or an image. For example, as illustrated in FIG. 4, the habit improving device 100 displays the target pattern of today and the distribution pattern of today, generates the advice information (in the example of FIG. 4, "Let's walk while going to work tomorrow early in the morning") regarding whether the activity amount is insufficient, and calculates the target pattern based on these patterns and/or the advice information when the target pattern calculation unit 306 calculates the target pattern after the next day.

(24:00 p.m.; bedtime) The habit improving device 100 may present the target pattern of the next day to the user using the output device 204 before the user goes to bed. The user is informed of the target pattern of the next day in advance so that it is expected that the user can smoothly perform activities of the next day. In addition, the output device 204 may present the advice information of "Let's walk while going to work tomorrow early in the morning" in the example of FIG. 4 to the user before going to bed.

[Operational Example: Entirety]

Next, using FIG. 5, an overview of the operational example of the habit improving device 100 will be described.

FIG. 5 is a flowchart showing an example of a processing procedure of the habit improving device 100. The processing procedure described below is merely an example, and each step of the processing may be changed as much as possible. In addition, regarding the processing procedure described below, steps can be suitably omitted, replaced, and added in accordance with the embodiment.

(Starting)

First, the user starts the habit improving device 100 via the input device 203. Moreover, inputs such as setting are received. The control unit 205 of the habit improving device 100 proceeds the processing in accordance with the following processing procedure.

(Step S501)

In Step S501, the control unit 205 operates as the attribute information acquisition unit 305 and acquires the attribute information of the user from the storage unit 202. For example, this attribute information is stored in the storage unit 202 in advance via the input device 203 or the communication interface 201. The user stores the attribute information of himself/herself in the storage unit 202 using the input device 203. In addition, the attribute information of the user may be present on a cloud, and the habit improving device 100 may acquire the attribute information therefrom via the communication interface 201 and store the acquired information in the storage unit 202. The attribute information is used in Step S504. Therefore, this Step S501 may be executed any time before Step S504.

(Step S502)

In Step S502, the control unit 205 operates as the activity amount acquisition unit 301, acquires the activity amount information (for example, data of the number of steps) from the activity amount meter 110 and/or the wristwatch-type wearable terminal 120 via the communication interface 201, and stores the activity amount information in the storage unit 202. For example, the activity amount acquisition unit 301 acquires the activity amount information for every hour and stores this activity amount information in the storage unit 202 together with time zone information.

(Step S503)

In Step S503, the control unit 205 operates as the distribution pattern calculation unit 302 and the group sorting unit 303. The distribution pattern calculation unit 302 acquires, from the storage unit 202, the activity amount information for every hour acquired by the activity amount acquisition unit 301 and calculates the distribution pattern in which this activity amount is made into a graph. Further, the group sorting unit 303 sorts a plurality of distribution patterns calculated by the distribution pattern calculation unit 302 into one or more groups. Further, the calculated distribution patterns are associated with the groups and stored in the storage unit 202.

(Step S504)

In Step S504, the control unit 205 operates as the external factor information acquisition unit 304, the attribute information acquisition unit 305, and the target pattern calculation unit 306. The external factor information acquisition unit 304 acquires the positional information of the user, the external factor information, and the schedule information of the user from the GPS reception unit 208 and the communication interface 201. The attribute information acquisition unit 305 acquires the attribute information of the user. The target pattern calculation unit 306 calculates the target pattern for each of the groups based on the attribute information of the user, the positional information, the external factor information, and the schedule information. The target pattern calculation unit 306 compares the calculated target pattern and the distribution pattern currently in progress to each other. Moreover, the target pattern may be updated. That is, for example, it may be compared to the target pattern every time the number of steps is acquired every hour, the target pattern may be reviewed every hour, and a target pattern for achieving a target number for the number of steps of one day may be generated based on the attribute information of the user, the external factor information, and the like.

(Step S505)

In Step S505, the control unit 205 operates as the advice presenting unit 307, compares the target pattern calculated by the target pattern calculation unit 306 and the latest distribution pattern calculated by the distribution pattern calculation unit 302 to each other, generates the advice information in accordance with the degree of achievement of the target, and presents the advice information to the user via the output device 204.

[Operational Example: S502]

Next, using FIGS. 6A and 6B, an example of Step S502 in FIG. 5 will be described.

(Step S601)

In Step S601, the control unit 205 operates as the activity amount acquisition unit 301 and acquires the activity amount information (for example, here, data of the number of steps) from the activity amount meter 110 and/or the wristwatch-type wearable terminal 120 via the communication interface 201.

(Step S602)

In Step S602, the control unit 205 operates as the activity amount acquisition unit 301 and stores information of the number of steps (acquired activity amount) in the storage unit 202. For example, the activity amount acquisition unit 301 acquires the activity amount information for every hour and begins to store this information in the storage unit 202. As illustrated in FIG. 6B, the activity amount acquisition unit 301 acquires a user ID (User ID) that can identify the user, the date when the activity amount is detected, and the day and the time from the activity amount meter 110 and/or the wristwatch-type wearable terminal 120 and stores information associated with each other together with the activity amount (this will be referred to as measurement information) in the storage unit 202. The table shown in FIG. 6B includes an example of measurement information.

When the activity amount meter 110 and/or the wristwatch-type wearable terminal 120 transmits the activity amount to the habit improving device 100 substantially at the same time as the activity amount is detected, the date, the day, and the time may be the date, the day, and the time when the activity amount acquisition unit 301 acquires the activity amount information via the communication interface 201. In this case, the habit improving device 100 acquires the date and the like using the timepiece device 206.

[Operational Example: S503]

Figure 7A:
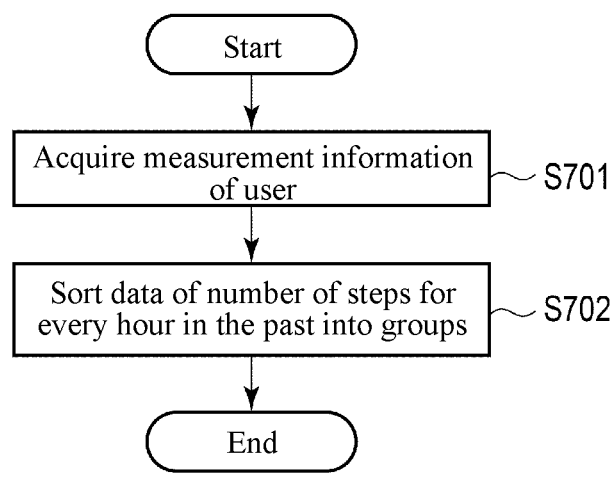
FIG. 7A is a flowchart schematically showing an example of the processing procedure of Step S503 in FIG. 5.

Next, using FIG. 7A, an example of Step S503 in FIG. 5 will be described.

(Step S701)

In Step S701, the control unit 205 operates as the distribution pattern calculation unit 302, and the distribution pattern calculation unit 302 acquires measurement information including the activity amount information for every hour acquired by the activity amount acquisition unit 301 from the storage unit 202 and calculates the distribution pattern in which this measurement information can be made into a graph.

(Step S702)

In Step S702, the control unit 205 operates as the group sorting unit 303, and the group sorting unit 303 sorts a plurality of distribution patterns calculated by the distribution pattern calculation unit 302 into one or more groups. Further, the group sorting unit 303 associates the calculated distribution patterns (for example, data of the number of steps for every hour for one day) with the groups and stores them in the storage unit 202. The group sorting unit 303 sorts a plurality of distribution patterns during a particular period in the past. The distribution pattern is data of the number of steps for each day. For example, the group sorting unit 303 sorts the data of the number of steps for one month in the past.

[Operational Example: S701 and S702]

Figure 7B:
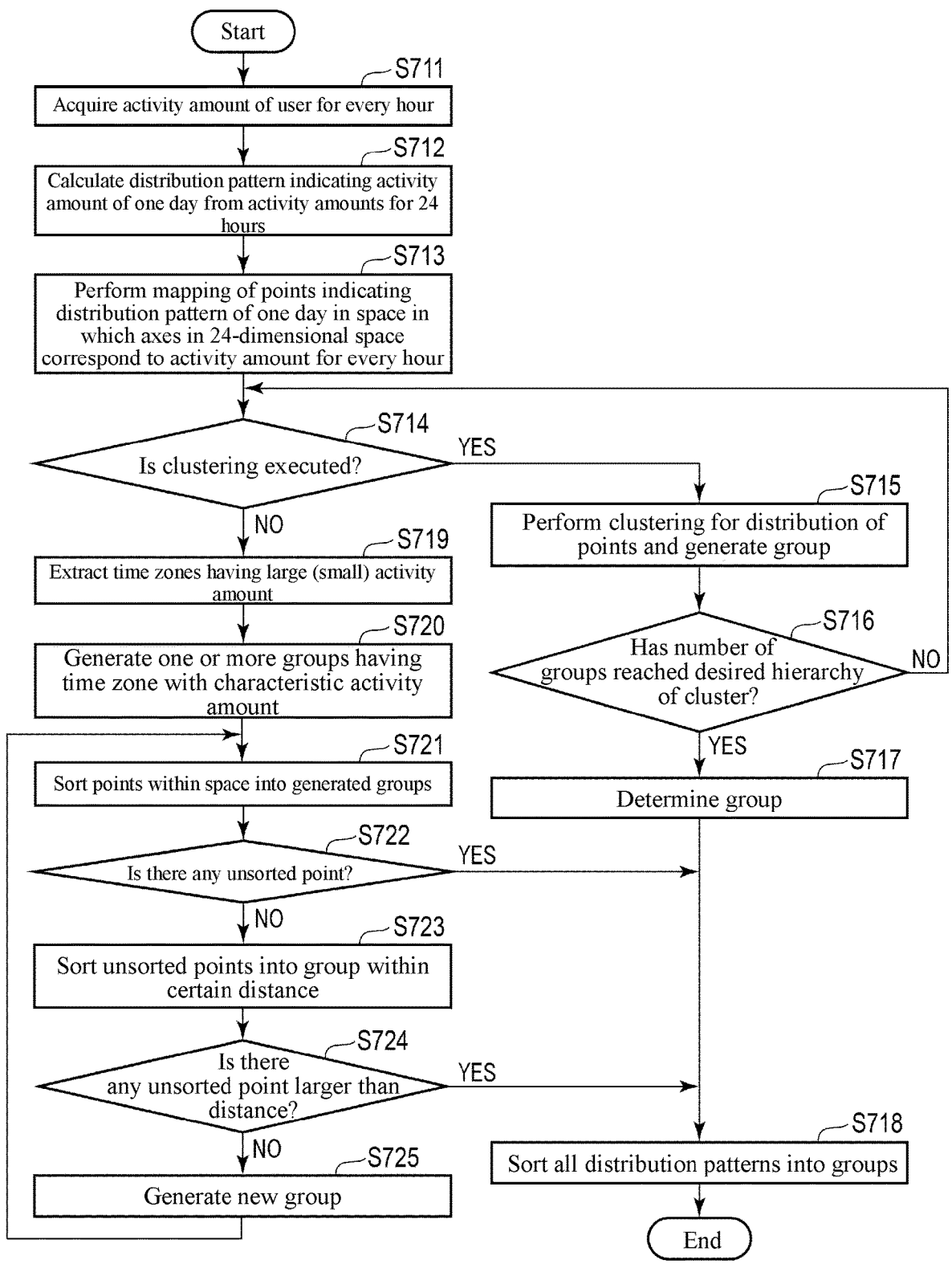
FIG. 7B is a flowchart schematically showing a specific example of the processing procedure of Steps S701 and S702 in FIG. 7A.

Next, using FIG. 7B, an example of detailed operation of Steps S701 and S702 in FIG. 7A will be described.

(Step S711)

In Step S711, the control unit 205 operates as the distribution pattern calculation unit 302 and acquires the activity amount information of the user for every hour from the storage unit 202 via the communication interface 201 through the activity amount meter 110 and/or the wristwatch-type wearable terminal 120.

(Step S712)

In Step S712, the control unit 205 operates as the distribution pattern calculation unit 302. Regarding the activity amount information acquired in Step S711, the control unit 205 calculates the distribution pattern in accordance with the date and the time when the activity amount meter 110 and/or the wristwatch-type wearable terminal 120 detects the activity amount or the date and the time when the habit improving device 100 acquires the activity amount. As a result, for example, the distribution pattern indicating change over time in the activity amount with respect to the time of one day from the activity amount for one day is calculated.

(Step S713)

In Step S713, the control unit 205 operates as the group sorting unit 303 and sorts a plurality of distribution patterns calculated by the distribution pattern calculation unit 302 into one or more groups. For example, the group sorting unit 303 performs mapping of the distribution pattern of the activity amount for 24 hours in a 24-dimensional space. In this 24-dimensional space, each axis corresponds to the activity amount for every hour. In other words, this space is a 24-dimensional space laid in a basis determined from vectors having the activity amount for every hour as components (24). Therefore, the distribution pattern of the activity amount in a certain day corresponds to one point within the 24-dimensional space. That is, a plurality of points corresponding to all the distribution patterns calculated by the distribution pattern calculation unit 302 are distributed in the 24-dimensional space. Regarding this point, it is assumed that even if only one of the activity amounts corresponding to the axes differs, the positions of the points in the 24-dimensional space differ, and the distribution patterns of the points become more similar to each other as the distance therebetween within the 24-dimensional space becomes shorter.

(Step S714)

In Step S714, the control unit 205 operates as the group sorting unit 303 and judges the way of grouping the points mapped in the 24-dimensional space. In the example of FIG. 7B, the control unit 205 judges whether the points mapped by the group sorting unit 303 is grouped by a technique based on clustering. Regarding this judgement, whether grouping is performed by a technique based on clustering is ordinarily set in advance by the user or at the time of design of the habit improving device 100. Whether the user uses clustering using the input device 203 of the habit improving device 100 may be able to be set, and it may judge whether clustering is executed by this setting in Step S714.

(Step S715)

In Step S715, the control unit 205 operates as the group sorting unit 303, groups the points distributed within the 24-dimensional space using a technique of clustering, and generates one or more groups. Here, description will be given on the assumption of hierarchical clustering that is one of the techniques of clustering. However, clustering is not limited to this technique, and division optimization clustering or the like may be used (however, a procedure for a change is generated).

(Step S716)

In Step S716, the control unit 205 operates as the group sorting unit 303 and judges whether the number of groups of the group generated in Step S715 corresponds to a desired hierarchy of the clusters. In Step S716, when it is judged that the number of groups corresponds to the desired hierarchy, the process proceeds to Step S717. On the other hand, when it is not judged in Step S716 that the number of groups corresponds to the desired hierarchy, the process returns to Step S714. In the case of an aggregation-type hierarchical clustering, from a state in which each of the points within the space is an individual cluster, these clusters are sequentially combined, and a hierarchy of the clusters is generated, and ultimately they are combined to one cluster. Here, a hierarchy indicates a state in which two clusters are combined, and the hierarchy changes as combining proceeds. For example, if the hierarchy of the clusters varies, the number of points included in the clusters varies.

In the case of a division-type hierarchical clustering, contrary to an aggregation-type hierarchical clustering, it is clustering in which dividing begins from one cluster. Dividing starts from a state in which an aggregation of data in its entirety is one cluster, these are sequentially divided, and the hierarchy of the clusters is generated.

In addition, Step S716, the group sorting unit 303 may judge whether the number of groups has reached a desired number. When it is judged that the number of groups has reached the desired number, the process proceeds to Step S717. On the other hand, when it is judged the number of groups has not yet reached the desired number, the process proceeds to Step S714.

(Step S717)

In Step S717, the control unit 205 operates as the group sorting unit 303 and determines the number of groups corresponding to the desired hierarchy judged in Step S716 and the groups corresponding to this number of groups.

(Step S718)

In Step S718, the control unit 205 operates as the group sorting unit 303, and each of the points in the space is sorted into any one of the groups determined in Step S717.

(Step S719)

In Step S719, the control unit 205 operates as the group sorting unit 303 and copes with a case in which one or more points distributed in the 24-dimensional space are grouped using a technique different from clustering (for example, hierarchy sorting). Herein, as an example, in order to perform sorting based on time zones at which the activity amount is large (and/or small), these time zones are extracted. The technique in Step S719 and thereafter differs from a technique based on clustering in that the features of the groups are set in advance and the points within the space are sorted based on the features.

(Step S720)

In Step S720, the control unit 205 operates as the group sorting unit 303 and generates one or more groups having characteristic time zones of the activity amount. For example, when the user has set such that the distribution patterns are considered to be the same during weekdays, when the group sorting unit 303 has a sorting criterion for the groups, such as the activity amount in the time zones at the daytime being equal to or larger than a first threshold and the activity amount in other time zones being equal to or smaller than a second threshold, for example, the distribution patterns belong to the same group. In addition, being different from this, for example, the average value (in addition, for example, a dispersion or a standard deviation may be calculated) for each time zone during weekdays is calculated from data of the distribution pattern of the user in the past. When a point corresponding to a certain distribution pattern is positioned within a space having a confidence level within 95% centering around the average value thereof, the group sorting unit 303 may sort this distribution pattern such that it belongs to the group during weekdays.

The groups generated by group sorting unit 303 correspond to a particular region within the space (for example, a 24-dimensional space), and the groups do not overlap each other. In addition, the group sorting unit 303 can make groups having various other features. For example, similar to that described above, the group sorting unit 303 can generate corresponding groups by setting a sorting criterion for capturing the features of the activity amount during a holiday.

(Step S721)

In Step S721, the control unit 205 operates as the group sorting unit 303 and sorts the points within the space into one or more groups generated in Step S720.

(Step S722)

In Step S722, the control unit 205 operates as the group sorting unit 303, and it is judged whether each of all the points distributed within the space belongs to any one of the groups generated in Step S721 and there is no unsorted point. When the group sorting unit 303 judges that there is an unsorted point in the groups, the process proceeds to Step S723. On the other hand, when it is judged that there is no unsorted point in the groups, the process proceeds to Step S718.

(Step S723)

In Step S723, the control unit 205 operates as the group sorting unit 303, and it is judged whether there is any of the groups generated in Step S720 within a distance set in advance from a point that is judged to be unsorted in any group. When there are two or more corresponding groups, the unsorted point is sorted into the closest groups (short distance) therein, and when there is one corresponding group, the unsorted point is sorted into the group.

The distance from the point within the space to the group has various definitions, and any definition may be adopted as long as it is uniquely determined and rational. For example, this distance is considered to be the shortest distance of the distances from the points within the space to the points belonging to the desired groups. In addition, the boundary of the group may be defined, and the distance from the points within the space to the boundary of the group may be defined as the distance between the point and the group. Here, the former definition will be employed. In Step S723, the group sorting unit 303 searches for the points at the shortest distance of the distances from the points judged to be unsorted in any group to the point belonging to a certain group and judges whether this distance is within the distance set in advance. When this distance is within the distance set in advance, this point judged to be unsorted is considered to belong to the group, and it is judged whether there is any other unsorted point.

(Step S724)

In Step S724, the control unit 205 operates as the group sorting unit 303 and judges whether or not there are any unsorted points at a distance larger than the distance set in advance in Step S723. When it is judged that there are no unsorted points at a distance larger than this distance, the process proceeds to Step S718. On the other hand, when there are unsorted points at a distance larger than this distance, the process proceeds to Step S725. Since unsorted points do not belong to any group, there is a need generate a new group including the unsorted points.

(Step S725)

In Step S725, the control unit 205 operates as the group sorting unit 303 and generates a group to include the points judged as unsorted points in Step S724, and the process returns to Step S721. For example, this generated group is a multi-dimensional sphere (for example, a 24-dimensional sphere) having the distance set in advance in Step S723 by the group sorting unit 303 (or a length shorter than this distance) as a radius and having dimensions of a space, and the points present in a region within this multi-dimensional sphere may be considered to be in the same group. If a group is generated in this manner, a generated group does not overlap other groups in region.

Here, an example in which the method of grouping one or more points within a space uses only one technique of a technique based on clustering and a technique not based on clustering such as hierarchy sorting, but both the techniques may be used. For example, there is a technique in which a plurality of groups in which the activity amount regarding one or more particular time zones is regulated is set in advance, and the points present in a region of the space not belonging to the groups are sorted into one or more groups through clustering.

Figure 7C:
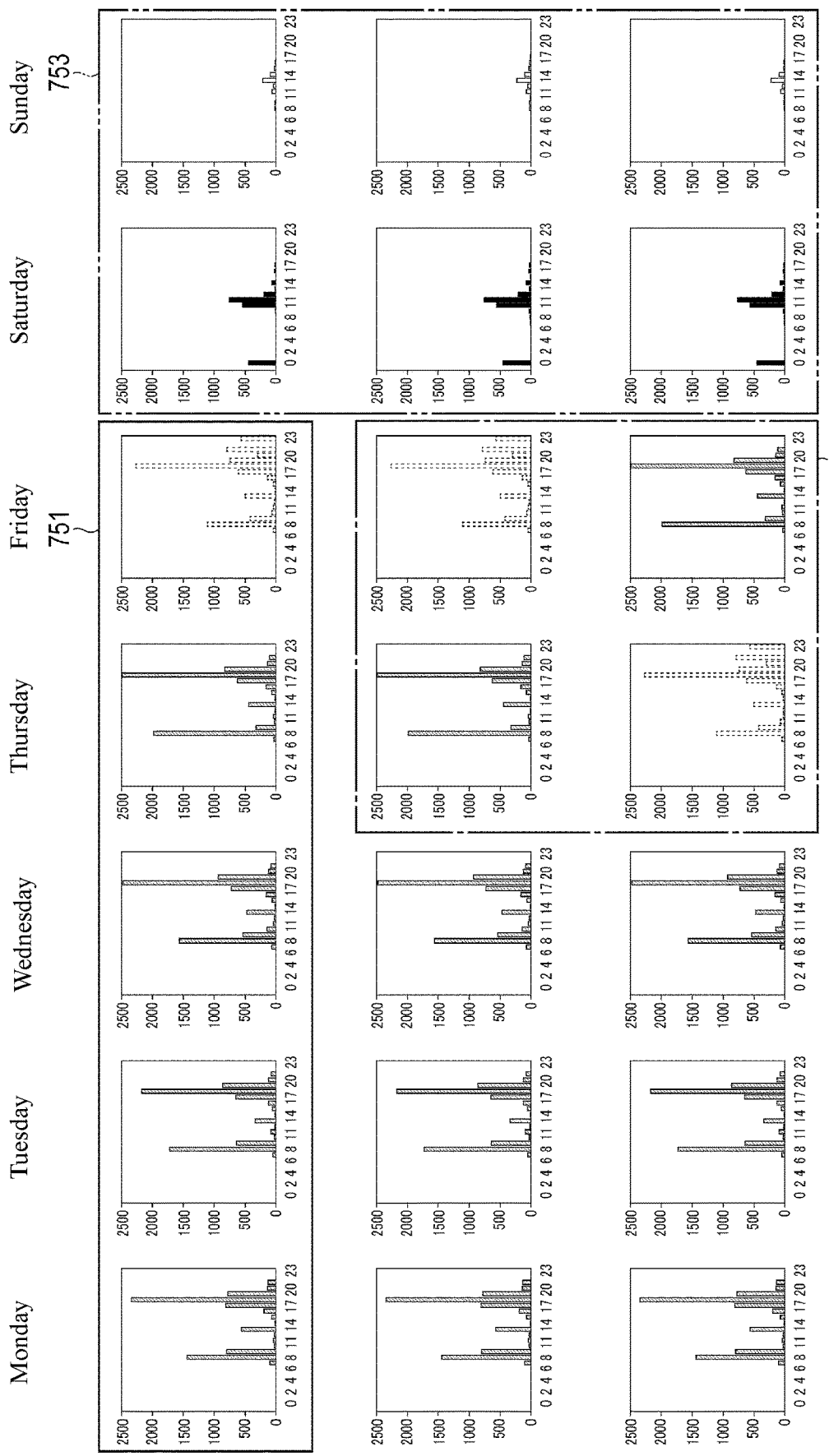
FIG. 7C is a view illustrating an example of distribution patterns obtained through the processing procedure in FIG. 7B and sorted groups thereof.

Next, using FIG. 7C, for example, a specific example of results when the distribution pattern is sorted into groups using the flowchart shown in FIG. 7B will be described. FIG. 7C illustrates the distribution pattern of the number of steps for three weeks united for each day, and this example is a case in which the distribution pattern is sorted into four groups.

In FIG. 7C, a different group is illustrated in a pattern of a different bar graph. In the example of FIG. 7C, it is sorted into the groups of four kinds, such as (1) a bar graph which has a contour surrounded by a line segment and of which the inner part is indicated by oblique lines, (2) a bar graph which has a contour surrounded by a dotted line and of which the inner part is indicated by a white space, (3) a bar graph which has a contour surrounded by a line segment and of which the inner part is indicated by a black space, and (4) a bar graph which has a contour surrounded by a line segment and of which the inner part is indicated by a white space. This example is not necessarily limited to having the same sorting results in a strict sense for those sorted through clustering, hierarchy sorting, or any other technique, but such results can be substantially obtained by any technique.

The bar graphs for five days during weekdays surrounded by a solid line frame 751 are in the same category such as weekdays but have different distribution patterns. Therefore, the distribution pattern from Monday to Thursday (corresponding to (1)) and the distribution pattern for Friday (corresponding to (2)) are sorted such that they belong to the different groups. For example, this grouping is judged depending on whether there is more activity amount than a predetermined value in the time zone set in advance as described in Steps S719, S720, and S721. In this case, for example, whether there is the activity amount (the number of steps) after 23:00 is one of the judgement criteria. That is, the number of steps on Friday within the solid line frame 751 is 500 steps or more after 23:00, and the number of steps from Monday to Thursday within the solid line frame 751 after 23:00 is fewer than 500 steps (zero steps in this example). Regarding this sorting, there is a probability that similar sorting is performed through clustering if the hierarchy of the clusters determined the number of groups is adjusted.

The bar graphs for four days surrounded by a single dashed line frame 752 are in the same day but have different distribution patterns. Therefore, it is clear that even if the day is the same, they are sorted to belong to the different groups. This grouping can also be performed by a technique similar to that of the foregoing grouping within the solid line frame 751. For example, the graph on the upper left and the graph on the lower right within the single dashed line frame 752 have a certain distribution pattern (corresponds to (1)) in which the number of steps after 23:00 is fewer than 500 steps, and the graph on the upper right and the graph on the lower left within the single dashed line frame 752 have a certain distribution pattern (corresponds to (2)) in which both the numbers of steps after 23:00 are 500 steps or more.

The bar graphs for six days surrounded by a double dashed line frame 753 are the same in the meaning of weekends, but since Saturday and Sunday have the different activity amounts in a particular time zone, the distribution pattern for Saturday (corresponds to (3)) and the distribution pattern for Sunday (corresponds to (4)) are sorted such that they belong to the different groups. This grouping can also be performed by a technique similar to that of the foregoing grouping within the solid line frame 751. For example, the number of steps on Saturday is 100 steps or more after 0:00, and the total number of steps from 10:00 to 13:00 is 1,000 steps or more. On the other hand, the number of steps on Sunday after 0:00 is fewer than 100 steps (zero steps), and the total number of steps from 10:00 to 13:00 is fewer than 1,000 steps.

[Operational Example: S504]

Figure 8A:
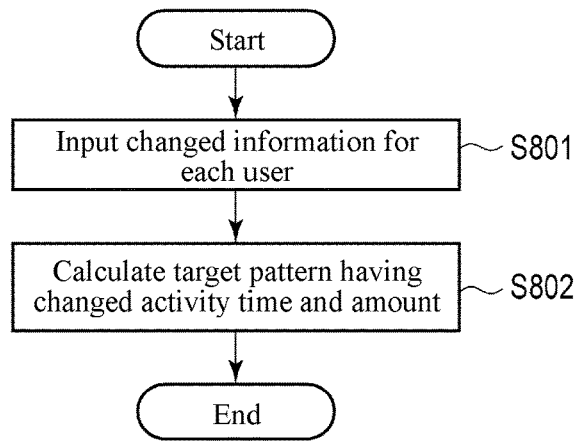
FIG. 8A is a flowchart schematically showing an example of the processing procedure of Step S504 in FIG. 5.

Next, using FIG. 8A, an example of Step S504 in FIG. 5 will be described.

(Step S801)

In Step S801, the control unit 205 operates as the external factor information acquisition unit 304 and the attribute information acquisition unit 305 and acquires the external factor information of the user and the attribute information of the user from the storage unit 202, the GPS reception unit 208, and/or the communication interface 201 for each user.

(Step S802)

In Step S802, the control unit 205 operates as the target pattern calculation unit 306, identifies a model pattern (or a basic pattern) typical for the group for each of the groups from the distribution pattern sorted into the group in Step S503 in accordance with the sorting technique through clustering, hierarchy sorting, or the like, and calculates the target pattern for each user for each of the groups based on the attribute information and the external factor information for each user acquired in Step S801 from this model pattern. When grouping is performed through a technique such as clustering, hierarchy sorting, or the like, a pattern typical for the group will be referred to as a model pattern. However, in the embodiment, for the sake of convenient identification, when grouping is performed when the number of distribution patterns which will become samples is equal to or smaller than the threshold, a pattern typical for the group will be referred to as a basic pattern.

[Operational Example: S802]

Figure 8B:
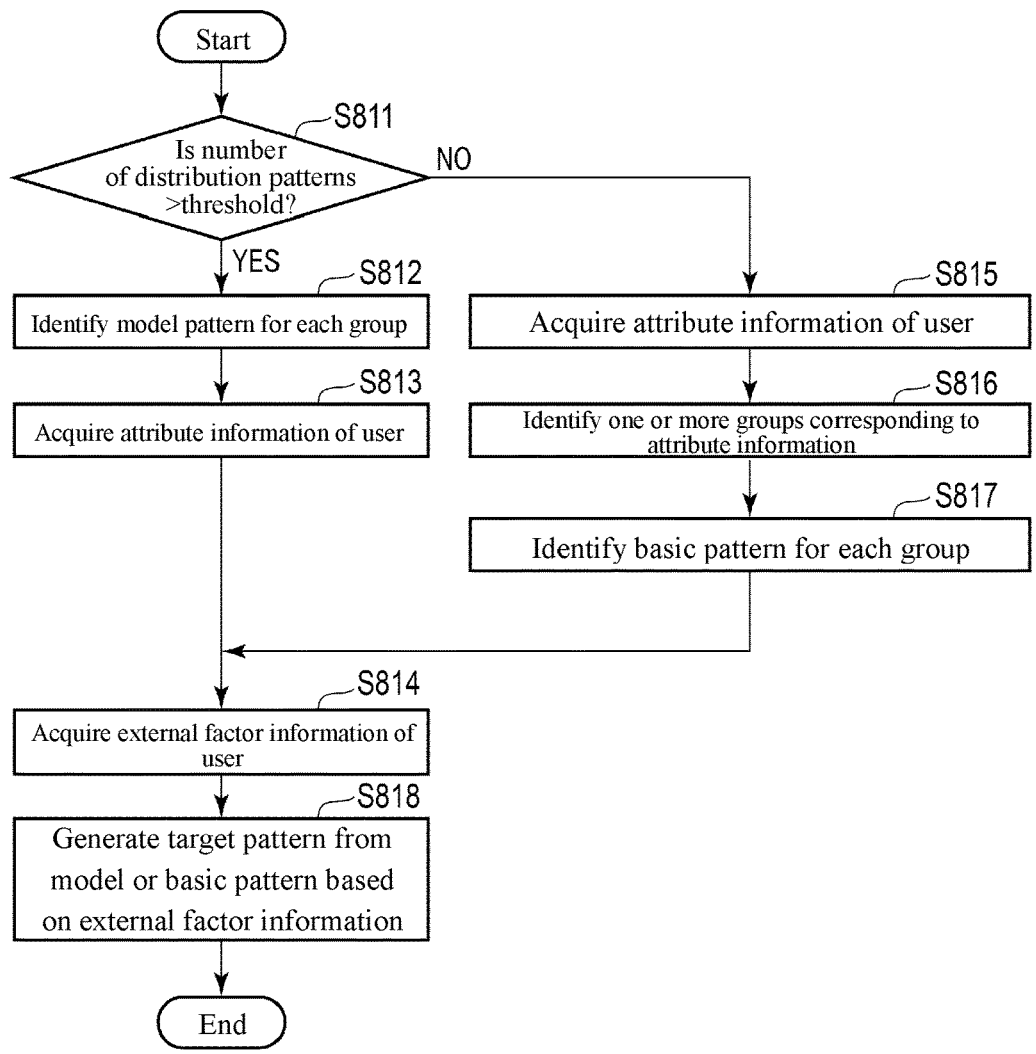
FIG. 8B is a flowchart schematically showing an example of the processing procedure of Step S802 in FIG. 8A.

Next, using FIG. 8B, an example of Step S802 in FIG. 8A will be described.

(Step S811)

In Step S811, the control unit 205 operates as the target pattern calculation unit 306 and judges whether the number of distribution patterns calculated in Step S503 is larger than the threshold. This threshold is a criterion whether the number of distribution patterns is sufficiently large to the extent that the features of the groups can be sorted and is ordinarily a numerical value set in advance. As the value of the threshold becomes large, it is assumed that the number of distribution patterns judged to have YES in this Step S811 increases and the feature of each of the groups becomes noticeable. Therefore, a more accurate target pattern can be obtained. For example, when the distribution pattern of the number of steps is acquired every day as in FIG. 7C, there is an example in which the threshold is set to 6, the process proceeds to Step S815 during first one week after starting to collect the samples of the number of steps, and the process proceeds to Step S812 from the second week.

In Step S812, the control unit 205 operates as the target pattern calculation unit 306 and identifies a model pattern that becomes a model of the group for each of the groups obtained through clustering, hierarchy sorting, or the like. That is, in the present embodiment, as the number of distribution patterns increases, the group can be sorted with high accuracy through clustering or the like and a more accurate target pattern can be obtained. When the number of distribution patterns which will become samples is larger than the threshold, a model pattern is acquired for each of the groups obtained by the technique through clustering or the like. Regarding identification of a model pattern, for example, a distribution pattern corresponding to a certain point at a position of the center or the center of gravity of the group from the pattern belonging to each of the groups is calculated as a model pattern by the target pattern calculation unit 306. In addition, being different from, the target pattern calculation unit 306 may randomly select a pattern from the distribution pattern belonging to the group and adopt this as a model pattern of a corresponding group.

In Step S813, the control unit 205 operates as the attribute information acquisition unit 305 and the target pattern calculation unit 306 and acquires the attribute information of the user from the storage unit 202.

In Step S814, the control unit 205 operates as the external factor information acquisition unit 304 and the target pattern calculation unit 306 and acquires the external factor information from the communication interface 201 and the GPS reception unit 208.

In Step S815, the control unit 205 acquires the attribute information of the user in a manner similar to that in Step S813.

In Step S816, the control unit 205 identifies one or more groups corresponding to the attribute information acquired in Step S815. Examples thereof include the physical information of the user, the residence information, the hobby information, and occupation information of occupation and a workplace. In addition to this, for example, if the user is a Japanese and an office worker, it is assumed that the group becomes different during weekdays and weekends. Therefore, three groups may be adopted for the attribute information of the user, as weekdays, Saturday, and Sunday. Moreover, when the user is regularly attending lessons, a sports gym, or the like, these can also be taken into account and the groups may be further increased.

In Step S817, the control unit 205 operates as the target pattern calculation unit 306, selects one pattern from the distribution pattern assumed for each of the groups identified in Step S816, takes this as the basic pattern, and identifies one basic pattern for each of the groups. An assumed distribution pattern may be able to be freely set by the user or the like as long as it belongs to the group and is set in accordance with the attribute information of the user. In addition, the target pattern calculation unit 306 may automatically generate the distribution patterns in accordance with the attribute information of the user and may take each of these distribution patterns as the basic pattern of the group.

In Step S818, the control unit 205 operates as the target pattern calculation unit 306 and generates a target pattern of the user from a model pattern of the user or the basic pattern based on the attribute information of the user and the external factor information.

Figure 8C:
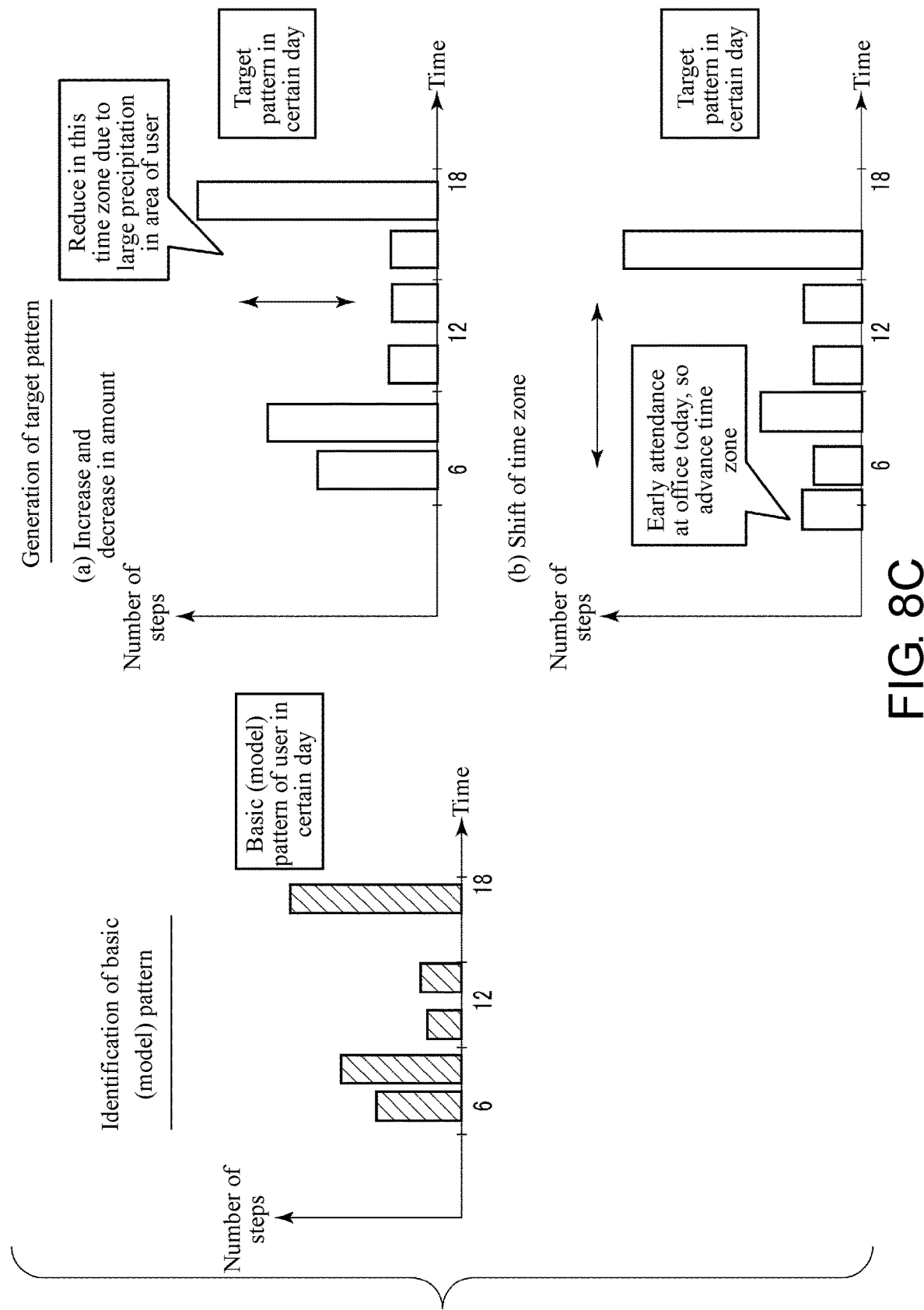
FIG. 8C is a view illustrating an example of a model pattern obtained in Step S812, a basic pattern obtained in Step S817, and a target pattern obtained in Step S818 in FIG. 8B.
Figure 8D:
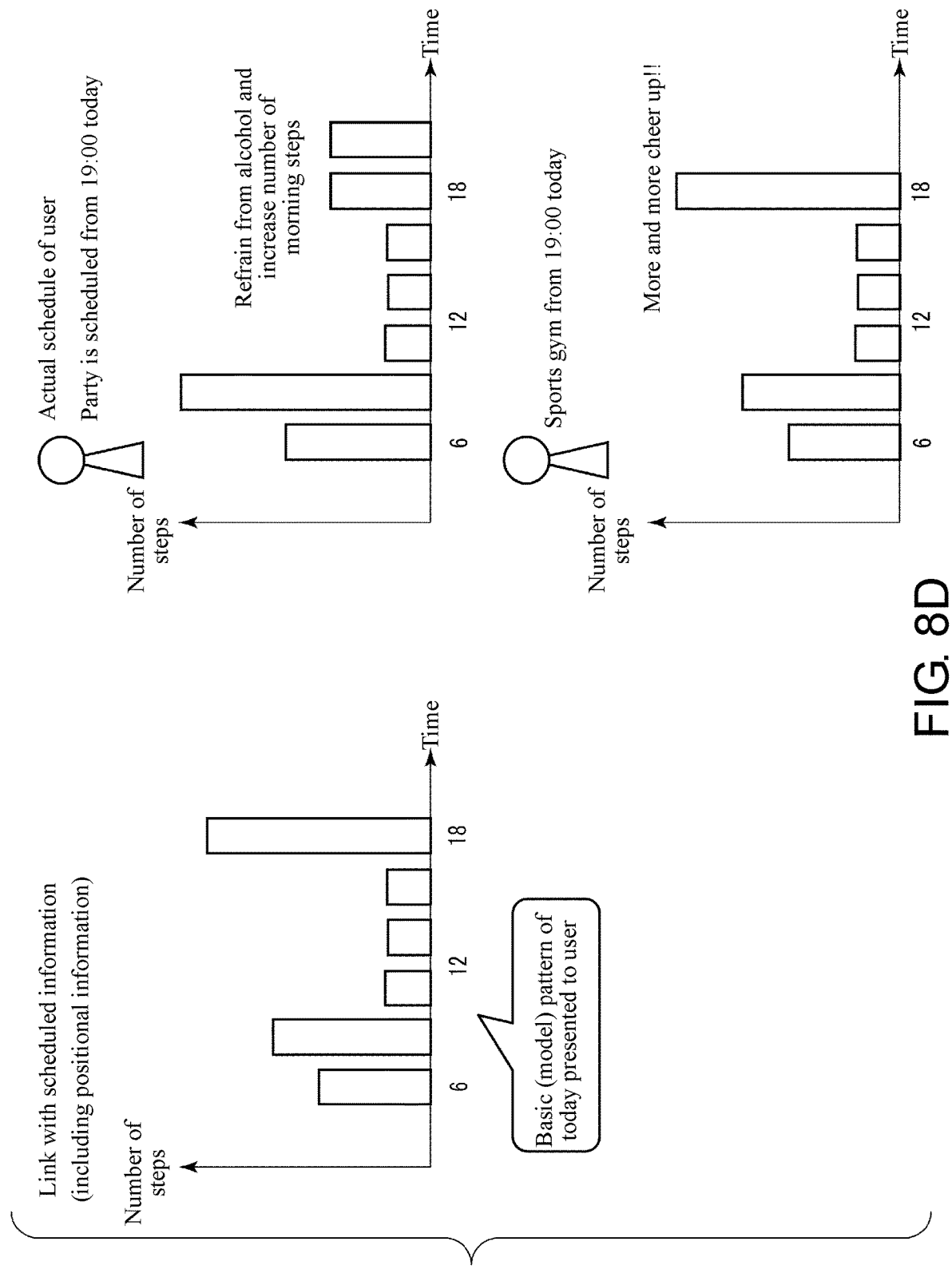
FIG. 8D is a view illustrating an example in which a target pattern is generated from the model pattern or the basic pattern in accordance with a schedule.

Next, with reference to FIGS. 8C and 8D, particular steps in FIG. 8B will be described. FIG. 8C illustrates the model pattern for each of the groups obtained by sorting the distribution patterns, or the basic pattern for each of the groups set based on the attribute information or the like of the user, and the target pattern for each user generated in accordance with the external factor information from the model pattern or the basic pattern. FIG. 8D illustrates an example of a case in which the activity amount is increased and decreased based on the schedule information of the user from the model pattern or the basic pattern or the activity time zone is shifted.

The model pattern identified in Step S812 or the basic pattern identified in Step S817 becomes as the distribution pattern illustrated on the left side in FIG. 8C, for example. That is, the target pattern calculation unit 306 identifies the model pattern or the basic pattern in a certain day based on the attribute information of the user.

Further, the target pattern calculation unit 306 acquires the external factor information as in Steps S814 and S818 and generates a target pattern based on this information.

In the example of (a) of FIG. 8C, the target pattern calculation unit 306 increases and decreases the activity amount based on the range of the user's behavior such as residence and a workplace of the user. In (a) thereof, in the area of this range of the user's behavior, it is already known that a precipitation is large in a particular time zone. Therefore, the activity amount (in this example, the number of steps) is reduced from the basic pattern or the model pattern in the particular time zone (from 12:00 to 14:00 in this example). Further, the reduced activity amount is allocated to another time zone (15:00 to 18:00 in this example from).

In the example of (b) of FIG. 8C, based on the schedule information of the external factor information, since this day is a day for early attendance at the office, the basic pattern or the model pattern is set for the entirety and the schedule is advanced in accordance with the time to attend the office. Further, the target pattern calculation unit 306 generates a target pattern of this day based on the basic pattern or the model pattern which have been advanced and further based on the external factor information or the attribute information.

In the example of FIG. 8D, as illustrated on the left side in the diagram, based on the basic pattern or the model pattern of today, the target pattern calculation unit 306 changes the activity time zone and the activity amount in accordance with the scheduled information of the user. The example in the upper right part of FIG. 8D is a case in which a party is scheduled from 19:00 today, and since the activity amount decreases at the time of the party, the target pattern calculation unit 306 generates a target pattern to increase the number of steps through extra walking or light jogging as much as the decreased activity amount at the time of going to the office in the morning.

In the example of on the lower right in FIG. 8D, since exercise at the sports gym is scheduled at 19:00 today, the target pattern calculation unit 306 generates a target pattern to increase the activity amount at the sports gym. In addition, since there is no need to reduce the activity amount other than the sports gym, the target pattern calculation unit 306 generates a target pattern on the assumption that there is no problem for other activities with the basic pattern or the model pattern.

Next, using FIG. 8E, a case in which when the user behaves differently from the scheduled information, the target pattern calculation unit 306 changes the target pattern in accordance with the behavior will be described.

The target pattern calculation unit 306 judges whether the user properly manages the schedule and changes the target pattern based on the behavior when the user behaves differently from the schedule. For example, the target pattern calculation unit 306 acquires the current activity amount from the activity amount acquisition unit 301, acquires the positional information and the schedule information of the user from the external factor information acquisition unit 304, and monitors the behavior of the user.

In addition, regarding activity amount information which is currently in progress, recent activity amount information, and/or current activity amount information, the activity amount information acquired by the activity amount acquisition unit 301 may be stored in the storage unit 202, and the target pattern calculation unit 306 may acquire the activity amount information thereof via the storage unit 202. The target pattern calculation unit 306 monitors the degree of achievement of the user in target pattern. When there is a separation between the target pattern and the actual distribution pattern, the target pattern may be changed to ensure the activity amount. In addition, even when the user suddenly changes the schedule, the target pattern calculation unit 306 may monitor the schedule and the activity amount thereof at all times. A case in which there is separation between the target pattern and the actual distribution pattern is a case, for example, in which the difference between the activity amounts of the target pattern and the actual distribution pattern in a certain time zone significantly deviates from the threshold.

Figure 8E:
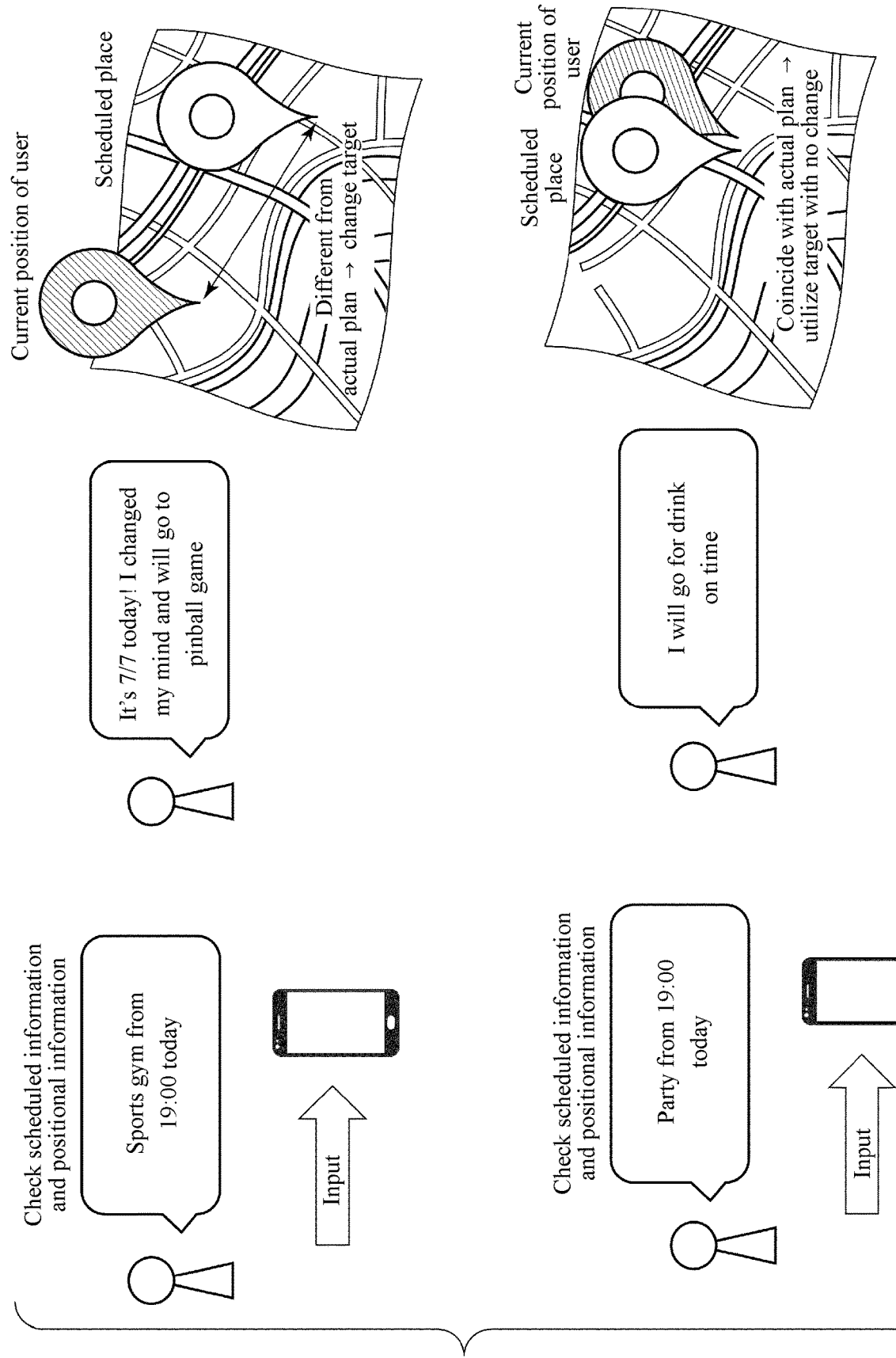
FIG. 8E is a view illustrating an example in which behavior of a user based on the schedule illustrated in FIG. 8D is checked depending on positional information.

The example in the upper part of FIG. 8E is an example in which the user is scheduled to go to the sports gym from 19:00 but the user has changed his/her mind and goes to play a pinball game. In this case, the target pattern calculation unit 306 judges that the user does not behave as scheduled based on the positional information and the schedule information of the user from the GPS reception unit 208. In this manner, the target pattern calculation unit 306 can automatically detect that the user is playing a pinball game based on the positional information, the activity amount information of the user, or the like. In this case, the target pattern calculation unit 306 changes the schedule from the sports gym to the pinball game and reschedules the reduced activity amount by transferring it to the schedule for the next day, for example.

The example in the lower part of FIG. 8E is an example in which the user is scheduled to go to a party from 19:00 and attends the party as scheduled. The target pattern calculation unit 306 checks for whether the user behaves as scheduled based on the positional information and the schedule information of the user from the GPS reception unit 208. In this case, since the user behaves as scheduled, the target pattern calculation unit 306 judges that there is no need to change the target pattern.

[Operational Example: S505]

Figure 9A:
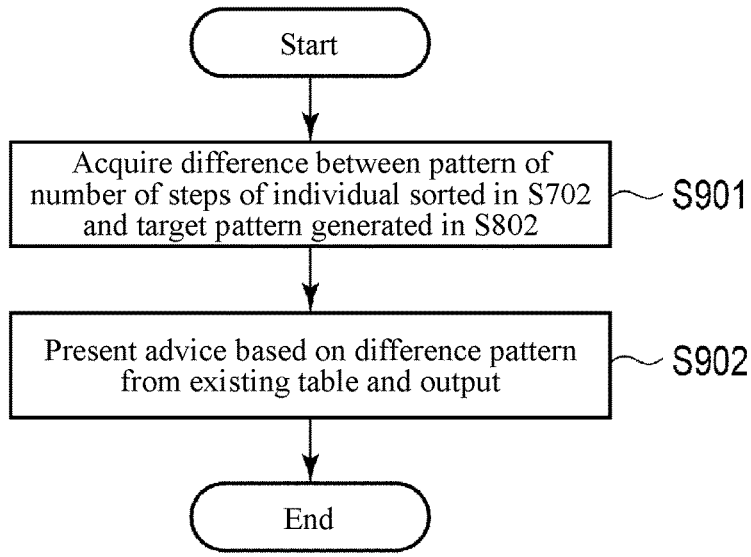
FIG. 9A is a flowchart schematically showing an example of the processing procedure of Step S505 in FIG. 5.

Next, using FIG. 9A, an example of Step S505 in FIG. 5 will be described.

(Step S901)

In Step S901, the control unit 205 operates as the advice presenting unit 307 and calculates the difference pattern by taking the difference between the distribution pattern currently in progress (for example, the distribution pattern from 0:00 a.m. until the present today) and the target pattern generated in Step S802 from the distribution pattern calculation unit 302. This difference pattern is a pattern in which the differences between the activity amounts in the distribution patterns and the activity amounts in the target patterns for each time are subjected to time distribution.

(Step S902)

In Step S902, the control unit 205 operates as the advice presenting unit 307, extracts the advice information from a table in the storage unit 202, in which the advice information corresponding to the difference pattern calculated in Step S901 is listed, and presents it to the user via the output device 204.

[Operational Example: S901 and S902]

Figure 9B:
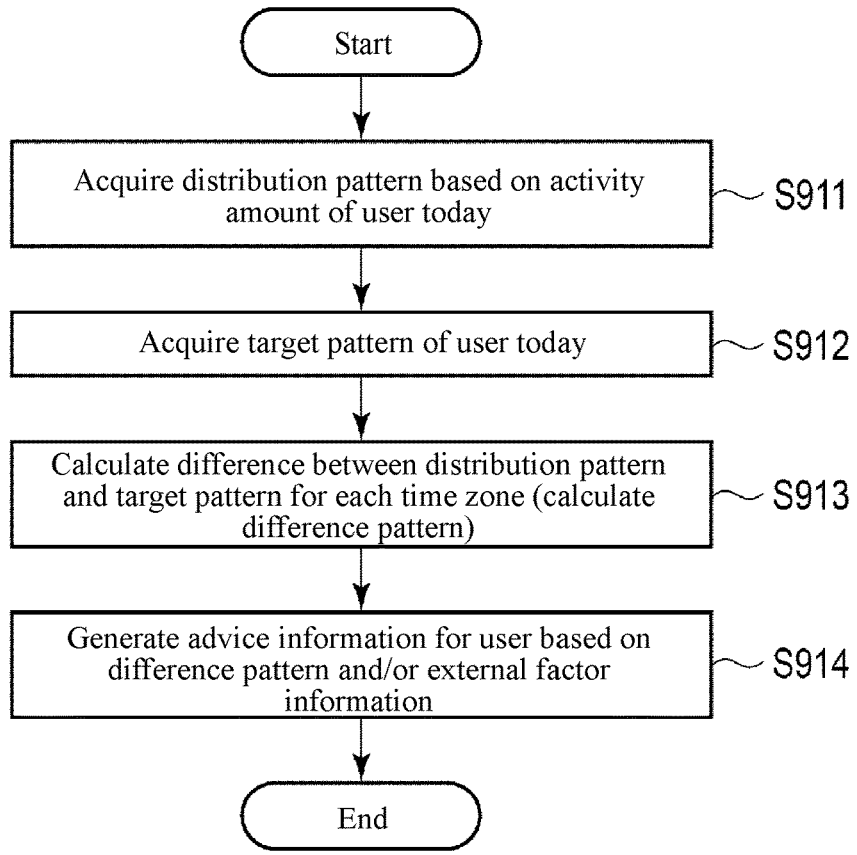
FIG. 9B is a flowchart schematically showing an example of the processing procedure of Step S901 in FIG. 9A.

Next, using FIG. 9B, an example of Steps S901 and S902 in FIG. 9A will be described.

(Step S911)

In Step S911, the control unit 205 operates as the advice presenting unit 307 and acquires the distribution pattern currently in progress calculated by the distribution pattern calculation unit 302 from the activity amount information acquired by the activity amount acquisition unit 301 via the communication interface 201. For example, this distribution pattern currently in progress is today's distribution pattern and is a distribution pattern for a period from the first time when the activity amount is acquired today until the present.

(Step S912)

In Step S912, the control unit 205 operates as the advice presenting unit 307 and acquires the target pattern of today from the target pattern calculation unit 306. The target pattern calculation unit 306 calculates the target pattern based on the external factor information, the attribute information, and the like of the user today.

(Step S913)

In Step S913, the control unit 205 operates as the advice presenting unit 307, obtains the difference between the activity amounts for each time zone by calculating the difference between the distribution pattern currently in progress today and the target pattern calculated in Step S912 for each of the time zones (the first period; for example, one hour), and calculates the difference pattern in which the differences are arranged throughout all the time zones.

(Step S914)

In Step S914, the control unit 205 operates as the advice presenting unit 307 and generates the advice information for the user based on the difference pattern calculated in Step S913 and/or the external factor information. For example, this advice information is stored in the storage unit 202 in association with the difference pattern. In addition, the advice presenting unit 307 may generate the advice information based on the state of the difference pattern. For example, the advice information is "a little short, take a walk a bit more later!" or the like when the difference pattern indicates a negative value (specifically, when the totaled amount of the activity amount of the target pattern is smaller than the totaled amount of the activity amount in the time zone corresponding to the distribution pattern) and is presented to the user in display, audio, or the like. Regarding another example of the advice information, when a party is scheduled in the schedule information from 19:00 today, an example of a wording presented to the user after waking up in the morning is "Refrain from drinking and increase a morning walk". Regarding another example, when attendance at the sports gym is scheduled in the schedule information from 19:00 today, there is a message of encouragement, such as recommendation for exercise at the sports gym.

In addition, the advice presenting unit 307 may generate the advice information for the user based on the external factor information. In the external factor information, for example, it is mainly assumed that the advice information is presented using the schedule information of the user and a weather forecast based on the positional information and the schedule information of the user. The target pattern calculation unit 306 gives this external factor information to the advice presenting unit 307 together with the reason for reference of the information which is referred to when the target pattern is calculated by the target pattern calculation unit 306. For example, when the weather forecast for the scheduled time zone at the scheduled site for running today is rainy, the target pattern calculation unit 306 calculates the target pattern such that the scheduled activity amount in the scheduled time zone for running is decreased and the activity amounts in other time zones are increased. In this case, the target pattern calculation unit 306 gives this information to the advice presenting unit 307, and the advice presenting unit 307 generates the advice information corresponding to this information and presents it to the user.

Furthermore, regarding an example of the advice information based on the schedule information, when a party is scheduled from 19:00 today, when attendance at the sports gym is scheduled from 19:00 today, or the like as described above, when the target pattern is calculated based on this schedule information, the target pattern calculation unit 306 gives reflecting information indicating how the schedule information is reflected in the target pattern to the advice presenting unit 307. The advice presenting unit 307 generates the advice information based on this reflecting information and presents it to the user.

Figure 9C:
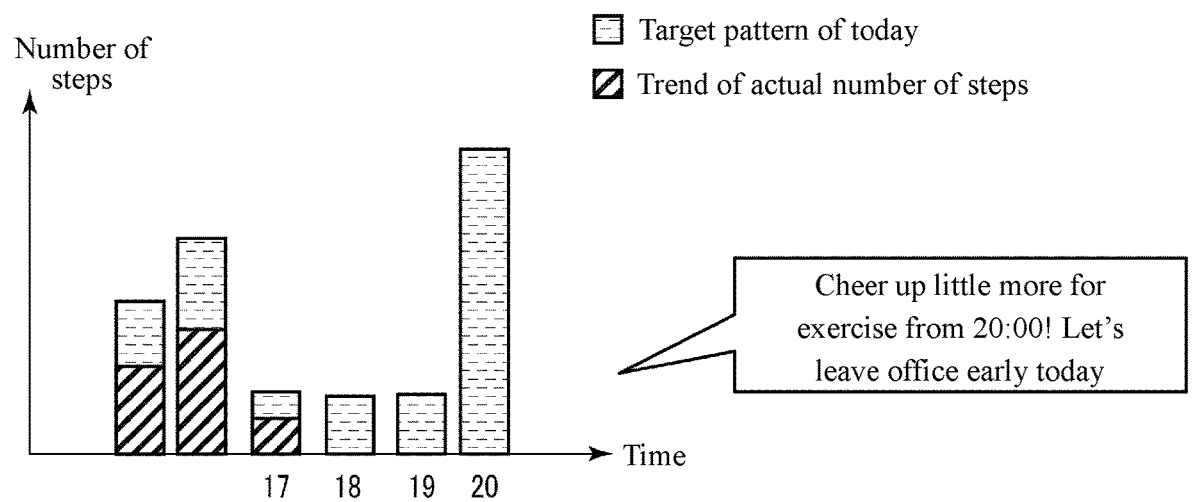
FIG. 9C is a view schematically illustrating an example of presenting of advice information obtained in Step S902 in FIG. 9A.

Next, using FIG. 9C, an example of the advice information presented by the advice presenting unit 307 will be described by describing the target pattern calculated by the target pattern calculation unit 306 and an actual distribution pattern currently in progress today.

The target pattern calculation unit 306 acquires the distribution pattern of the activity amount before 18:00 from the storage unit 202 or the activity amount acquisition unit 301. Moreover, the target pattern calculation unit 306 makes the target pattern at the current time (18:00 in the example of FIG. 9C) based on information from the group sorting unit 303 and the external factor information acquisition unit 304. Since the activity amount before the current time in the target pattern in FIG. 9C is smaller than the activity amount of the target pattern, it is recommended to go home early and go to the sports gym or the like for exercise from 20:00 (reflecting information). The target pattern calculation unit 306 gives this reflecting information to the advice presenting unit 307, and the advice presenting unit 307 generates the advice information such as "Cheer up a little more for exercise from 20:00! Let's leave the office early today", for example, based on this reflecting information and presents it to the user. In addition, reflecting information and the advice information may be stored in the storage unit 202 in association with each other, and the advice presenting unit 307 may acquire the advice information from the storage unit 202 based on the reflecting information received from the target pattern calculation unit 306.

[Operation and Effects]

As above, the habit improving device 100 of the present embodiment records the information of the number of steps for every hour acquired in Step S502 and calculates the distribution pattern of the number of steps of one day based on the information of the number of steps in Step S503. Further, the habit improving device 100 sorts a plurality of distribution patterns calculated by the distribution pattern calculation unit 302 into groups through clustering, hierarchy sorting, and/or the like by the group sorting unit 303. Moreover, in Step S504, the target pattern that becomes a target desirable for the user for each of the groups is calculated by the target pattern calculation unit 306 based on the attribute information of the user and the external factor information. This target pattern is calculated based on the attribute information of the user and the external factor information. Therefore, since the features of the user are sorted based on the groups, and furthermore, the attribute information of the user from which information is not easily extracted simply with the distribution pattern is included, the habit improving device 100 can calculate a target pattern effective for the user. Moreover, the target pattern is also calculated based on the external factor information of the user and is calculated based on an external factor such as an environment other than the user himself/herself. For this reason, since calculation is performed including the external factor information which cannot be extracted simply with the distribution pattern and which cannot be extracted even if the attribute information of the user and the distribution pattern are combined, the habit improving device 100 can further calculate a target pattern effective for the user with higher accuracy.

Moreover, in Step S505, the advice presenting unit 307 can present appropriate advice information to the user in association with the schedule information of the user, for example, based on the calculated target pattern. Moreover, the target pattern calculation unit 306 can revise and/or change the target pattern as required based on the distribution pattern currently in progress and the target pattern corresponding to this distribution pattern, and when the target pattern is revised and/or changed, the advice presenting unit 307 presents the advice information corresponding to the revision and the change to the user. As a result, according to the habit improving device 100, the user can appropriately receive the advice information regarding activities at a suitable timing, and thus a possibility of achieving the target pattern can be enhanced.

Modification Example

Hereinabove, the embodiment of the present invention has been described in detail, but the foregoing description is merely an example of the present invention in every respect. It goes without saying that various improvements or modifications can be performed without departing from the scope of the present invention. For example, the following changes can be made. In addition, when the present invention is performed, a specific constitution according to the embodiment may be suitably employed. Hereinafter, similar reference signs are used for constituent elements similar to those in the foregoing embodiment, and description of points similar to those in the foregoing embodiment is suitably omitted. The following modification examples can be suitably combined.

<1>

The external factor information acquisition unit 304 may acquire the attribute information of another user other than the user (as described above, for example, information including age, residence, a gender, and/or the like) and a target pattern of this user and may match the attribute information of the user himself/herself acquired by the attribute information acquisition unit 305 and the attribute information of another user (for example, executed by the target pattern calculation unit 306). When the degree of matching is higher than the judgement criterion set in advance, this target pattern of another user may be employed.

Therefore, since effects similar to those in the case in which a number of similar distribution patterns are sampled can be achieved by referring to the similar attribute information of another user, a target pattern of the user can be accurately calculated. As a result, the habit improving device of the present embodiment can present more appropriate advice information to the user.

Moreover, in this case, if there is an actual sample in which another user has achieved the target pattern, it is desirable to make the target pattern more likely to be employed (for example, increase the weighting). It is possible to expect that the user is more likely to achieve this target pattern compared to a case of employing other target patterns which has not been achieved.

<2>

With reference to the distribution pattern of another user having similar attribute information and the schedule information, in order to come closer to the attribute which has already been realized by another user, it is considered that the user himself/herself efficiently realizes a desired attribute using the distribution pattern and/or the target pattern of another user. In order to realize this, first, an attribute which the user himself/herself intends to realize is set, and another user already having this attribute intended to be realized (for example, a blood pressure value or a BMI value) and having other attributes similar to the attributes of the user himself/herself is found from a database or the like. For example, finding the attributes of another user is realized by searching for the attributes using the attribute information acquisition unit 305 connected to the server 130 via the communication interface 201. In this case, the server 130 may store the attribute information, the external factor information, and information of the distribution pattern and the target pattern from a number of users.

It is effective for the user to simply read and refer to the distribution pattern and/or the target pattern which has been searched for in this manner. However, moreover, this pattern may be employed as a target pattern, the target pattern calculation unit 306 may calculate the target pattern as described in the foregoing embodiment, and furthermore, the advice presenting unit 307 may present the advice information to the user.

If there is such a system, in order for the user to realize a target attribute (for example, the user realizes an ideal body type), an actual distribution pattern (a distribution pattern of another user) for a distribution pattern to be realized can be adopted as a standard, and thus a possibility of being capable of accurately calculating the target pattern to be realizing can be increased.

In addition, it is desirable that the difference between the attribute information of the user of the target pattern before being realized by the user and the attribute information of the user after the target pattern is realized be stored in a server or the like for each user as the attribute information for each item of the attribute information. In this case, another user having the attribute information desired by the user himself/herself can be efficiently found from the attribute information similar to that of the user himself/herself based on the current attribute information of the user himself/herself and the attribute information intended to be realized, by searching for similar attribute information of another user with reference to the server. Accordingly, since the user himself/herself can efficiently find and utilize an effective target pattern of another user, it is easy for the user himself/herself to reach a desired attribute. According to this constitution, for example, since a person in his/her forties desiring to have a slender build has a number of such lifestyle habits (corresponding to the attribute information, and the distribution pattern and/or the target pattern), it is possible to appropriately present to the user that it is better to have different exercise habits (corresponding to the distribution pattern).

<3>

For example, in Step S719 and thereafter in FIG. 7B, the points within the space may be sorted into groups in the following manner.

For example, when it becomes clear based on the attribute information of the user that the user is at work during weekdays and spends a particular time zone at a particular place, the group sorting unit 303 estimates that substantially the same distribution pattern is indicated during weekdays, calculates the average value for each time zone during weekdays, and sets the distribution pattern having the average value as one of the basic patterns. The group sorting unit 303 can make a basic pattern having various other features. The group sorting unit 303 can generate the basic pattern for a holiday in a manner similar to that described above.

For example, the group sorting unit 303 may sort the distribution patterns by making the groups as follows even if a basic pattern is not introduced. For example, the group sorting unit 303 divides the groups depending on whether the activity amount at late night (for example, after 23:00 until 2:00 the next day) during weekdays is larger than the first threshold (for example, a value larger than the average value of the activity amount during weekdays by 50%). Regarding the activity amount and the time zone thereof, many criteria are set, and a plurality of groups is sorted using these criteria at the same time. For example, when sorting is performed with criteria of two ways such as whether the entire activity amount is smaller than the second threshold (for example, 50% of the activity amount during weekdays), and whether the activity amount at late night during weekdays is larger than the first threshold, sorting of 2×2=4 groups can be performed due to the first and second thresholds. A different criterion other than these criteria for the activity amount may be introduced, and the points within the space may be sorted including these criteria. For example, a criterion for distinguishing weekdays (from Monday through Friday), weekends, and national holidays may be introduced. In addition, when it becomes clear that behavior on Friday differs from that during weekdays, Friday may be sorted into a group different from that for weekdays.

<4>

The group sorting unit 303 may perform sorting of groups based on the plurality of model patterns which is a typical pattern of the group and set in advance. In this constitution, the group sorting unit 303 sorts a plurality of distribution patterns into groups using a model pattern indicating the features of the groups thereof for each of the groups and set in advance. The feature is that a model pattern is set in advance, and a setter such as a user can set a model pattern in advance. Therefore, when a plurality of distribution patterns of the user is sorted into groups, it is possible to realize grouping in which a significance is given clearly.

<5>

Although it is not illustrated, the activity amount meter 110, the wristwatch-type wearable terminal 120, and/or the habit improving device 100 may include an acceleration sensor, a pressure sensor, a gyro-sensor, and/or a magnetic field sensor.

An acceleration sensor is a sensor for detecting an acceleration. For example, it is a three-axis acceleration sensor and detects an acceleration of the sensor regarding linear independent three axes (for example, three axes orthogonal to each other). Further, the acceleration sensor outputs an acceleration signal expressing accelerations in three directions to the control unit 205. The acceleration sensor can obtain a roll angle and a pitch angle from a value of an acceleration at the time of a standstill.

A pressure sensor is a general sensor for detecting a pressure. For example, according to the pressure sensor, an elevation of the user can be detected by measuring an air pressure.

A gyro-sensor is a general sensor capable of detecting an angular speed of the sensor. For example, it is a three-axis gyro-sensor and detects an angular speed of the sensor regarding linear independent three axes. The gyro-sensor outputs an angular speed signal expressing angular speeds in three directions to the control unit 205.

A magnetic field sensor is a general sensor and is used for judging a posture of the user. For example, the magnetic field sensor is a three-axis magnetic field sensor and detects the intensity of geomagnetism around the sensor regarding three axes including the direction and the intensity (magnitude).

The control unit 205 may obtain an angle by integrating an angular speed from initial posture information of the user using a technique of correcting an error due to a drift for the angular speed obtained from the gyro-sensor from information of the acceleration sensor and the magnetic field sensor, and may obtain a posture angle for each of the sensors at a desired time elapsed from the initial time. Regarding an initial posture, the roll angle and the pitch angle can be obtained using the acceleration sensor. A yaw angle can be obtained using the magnetic field sensor.

Three-dimensional components of a magnetic field in which a tilt error is corrected are calculated from the three-dimensional components of a magnetic field obtained by the magnetic field sensor, and the roll angle and the pitch angle which have been previously obtained. A yaw angle can be calculated from an x component and a y component of the three-dimensional components of the magnetic field in which this tilt error is corrected. When the user has moved from the initial posture, an angle is obtained by performing time integration of the angular speed, and thus a posture angle for each of the sensors at an arbitrary time can be obtained based on the initial posture and the elapsed time period.

Based on change in posture angle, movement (for example, movement of an arm and/or a leg) when the user is at a standstill can be detected. For example, a position of the user seldom changes but performs exercise (for example, dance or exercise at the sports gym), the position can be more correctly detected by comparing the case in which these are not detected.

<6>

The device of the present invention can also be realized by a computer and a program. The program can be recorded in a recording medium (or a storage medium) and can also be provided through a network.

In addition, each of the devices and device parts thereof described above can be operated by any of a constitution of hardware or a combined constitution of a hardware resource and software. Regarding software of a combined constitution, a program for causing the computer to realize operation (or functions) of each of the devices is used by being installed in a computer in advance from a network or a computer readable recording medium (or a storage medium) and executed by a processor of the computer.

<7>

This invention is not limited to the foregoing embodiment as it stands, and the constituent elements can be modified and specified in the performing stage within a range not departing from the gist thereof. In addition, various inventions can be formed by a suitable combination of a plurality of constituent elements disclosed in the foregoing embodiment. For example, some constituent elements may be removed from all the constituent elements described in the embodiment. Moreover, constituent elements in a different embodiment may be suitably combined.

In addition, "and/or" denotes one or more arbitrary items of items enumerated with "and/or" therebetween. Regarding a specific example, "x and/or y" denotes any element of an aggregation {(x), (y), (x, y)} constituted of three elements. Regarding another specific example, "x, y, and/or z" denotes any element of an aggregation {(x), (y), (z), (x, y), (x, z), (y, z), and (x, y, z)} constituted of seven elements.

APPENDIX 1

There is provided a habit improving device (100) including first calculation units (301 and 302) which acquire, for each of first periods, a user's activity amount totaled for each of the first periods and calculate a distribution pattern indicating change over time in the activity amount during a second period including the first periods; a sorting unit (303) which sorts a plurality of the distribution patterns into one or more groups; second calculation units (304, 305, and 306) which calculate, based on a factor other than the activity amount, a target pattern that becomes a target for the user in association with the groups; and a presenting unit (307) which presents advice information to the user based on the current distribution pattern and the target pattern.

The invention claimed is:

1. A habit improving device comprising:
   an activity amount meter, comprising an acceleration sensor, configured to measure an activity amount of a user using the acceleration sensor;
   a positional sensor, configured to locate position information of the user; and
   a processor, configured to:
     acquire an input comprising the activity amount of the user for each of a plurality of first periods from the activity amount meter and acquire the position information of the user for each of the plurality of first periods from the position sensor;
     determine a distribution pattern to the input indicating change over time in the activity amount for each of the plurality of first periods within a second period;
     sort the input that is expressed by the plurality of distribution patterns based on a similarity of the plurality of the distribution patterns into one or more groups of the distribution patterns;
     determine a target pattern that becomes a target for the user for each of the groups, based on attribute information relating to an attribute of the user and external factor information relating to an external factor that is a factor affecting the user due to a matter other than the user, wherein the external factor information comprises position information of the user for each of the plurality of first periods and schedule information relating to a schedule of the user;

judge whether the user has deviated from a position scheduled in accordance with the schedule in the schedule information and change the target pattern in accordance with a deviated position when it is judged that the user has deviated, comprising to:

acquire a distribution of a plurality of vectors from the plurality of the distribution patterns, the vector having an activity amount for each of the plurality of first periods as a component, and one vector corresponding to one distribution pattern within the second period for each of the plurality of second periods; and perform sorting by clustering a plurality of points into one or more groups based on positions of the plurality of points within a space laid in a basis determined from the component while the points within the space correspond to the vectors;

compare distances between a certain point and other points within the space to each other and perform grouping such that two points at the shortest distance belong to the same group; and compare distances between a point belonging to a certain group and a plurality of points belonging to other groups and perform grouping of groups of the points at the shortest distance as the same group when the shortest distance of the distances is equal to or smaller than a threshold; and output to a display an advice information together with the changed target pattern to the user relating to activity for the user to perform for achieving the changed target pattern based on the position information and the schedule information of the user as well as a difference between a current distribution pattern and the changed target pattern, wherein the advice information includes activity for the user to perform for achieving the target pattern, so as to improve habits of the user.

2. The habit improving device according to claim 1, wherein the processor uses at least one of physical information, residence information, occupation, a workplace, hobbies, and favorite food and drink of the user as the attribute information.

3. The habit improving device according to claim 1, wherein the processor is further configured to use weather forecast information based on the positional information as the external factor information.

4. The habit improving device according to claim 1, wherein the processor is further configured to present the current distribution pattern and a target pattern corresponding to the current distribution pattern in a comparable state to the user as the advice information.

5. The habit improving device according to claim 1, wherein the processor is further configured to use at least one of an amount of consumed energy consumed by the user and the number of steps of the user as the activity amount.

6. The habit improving device according to claim 1 further comprising:

the processor is further configured to generate, for each of the groups, one of the distribution patterns belonging to the groups as a model pattern that is a typical pattern of the groups.

7. The habit improving device according to claim 1, wherein the processor is further configured to sort a plurality of the distribution patterns into the groups based on a plurality of the model patterns set in advance.

8. The habit improving device according to claim 1, wherein the processor is further configured to sort a plurality of the distribution patterns into the groups based on whether an activity amount of the distribution pattern in a particular time zone is equal to or larger than a threshold.

9. A non-transient computer-readable recording medium, recording a program for causing a computer to function as each unit included in the habit improving device according to claim 1.

10. A habit improving method, applicable to a habit improving device comprising a processor, a positional sensor, and an activity amount meter having an acceleration sensor, comprising:

measuring, by using the acceleration sensor of the activity amount meter, an activity amount of a user;

locating, by using the positional sensor, position information of the user;

acquiring, by the processor, an input comprising the activity amount of the user for each of a plurality of first periods from the activity amount meter and acquiring, by the processor, the position information of the user for each of the plurality of first periods from the position sensor;

determining, by the processor, a distribution pattern to the input indicating change over time in the activity amount for each of the plurality of first periods within a second period;

sorting, by the processor, the input that is expressed by the plurality of distribution patterns based on a similarity of the plurality of the distribution patterns into one or more groups of the distribution patterns;

determining, by the processor, a target pattern that becomes a target for the user for each of the groups, based on attribute information relating to an attribute of the user and external factor information relating to an external factor that is a factor affecting the user due to a matter other than the user, wherein the external factor information comprises position information of the user for each of the plurality of first periods and schedule information relating to a schedule of the user;

judging, by the processor, whether the user has deviated from a position scheduled in accordance with the schedule in the schedule information and changing, by the processor, the target pattern in accordance with a deviated position when it is judged that the user has deviated, comprising:

acquiring, by the processor, a distribution of a plurality of vectors from the plurality of the distribution patterns, the vector having an activity amount for each of the plurality of first periods as a component, and one vector corresponding to one distribution pattern within the second period for each of the plurality of second periods;

performing, by the processor, sorting by clustering a plurality of points into one or more groups based on positions of the plurality of points within a space laid in a basis determined from the component while the points within the space correspond to the vectors, comparing, by the processor, distances between a certain point and other points within the space to each other and performing, by the processor, grouping such that two points at the shortest distance belong to the same group; and comparing, by the processor, distances between a point belonging to a certain group and a plurality of points belonging to other groups and performing, by the processor, grouping of groups of the points at the shortest distance as the same group when the shortest distance of the distances is equal to or smaller than a threshold; and outputting, by the processor, to a display an advice information together with the changed target pattern to the user relating to activity for the user to perform for achieving the changed target pattern based on the position information and the schedule information of the user as well as a difference between a current distribution pattern and the changed target pattern, wherein the advice information includes activity for the user to perform for achieving the target pattern, so as to improve habits of the user.

* * * * *